US010611795B2

(12) United States Patent
Fisher et al.

(10) Patent No.: US 10,611,795 B2
(45) Date of Patent: Apr. 7, 2020

(54) METHODS FOR VIRAL INACTIVATION USING ECO-FRIENDLY DETERGENTS

(71) Applicant: Genentech, Inc., South San Francisco, CA (US)

(72) Inventors: Susan Fisher, San Carlos, CA (US); Qi Chen, Hillsborough, CA (US); Lenore Norling, Pleasanton, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/154,235

(22) Filed: May 13, 2016

(65) Prior Publication Data

US 2016/0333046 A1 Nov. 17, 2016

Related U.S. Application Data

(63) Continuation of application No. PCT/US2014/065391, filed on Nov. 13, 2014.

(60) Provisional application No. 61/937,284, filed on Feb. 7, 2014, provisional application No. 61/905,075, filed on Nov. 15, 2013.

(51) Int. Cl.
| | | |
|---|---|---|
| C07K 1/18 | (2006.01) | |
| A61K 38/00 | (2006.01) | |
| C07K 1/22 | (2006.01) | |
| C07K 1/36 | (2006.01) | |
| C07K 14/435 | (2006.01) | |
| C07K 1/14 | (2006.01) | |
| A61L 2/00 | (2006.01) | |

(52) U.S. Cl.
CPC ............ *C07K 1/36* (2013.01); *C07K 1/14* (2013.01); *C07K 1/18* (2013.01); *C07K 1/22* (2013.01); *A61K 38/00* (2013.01); *A61L 2/0088* (2013.01); *A61L 2202/21* (2013.01)

(58) Field of Classification Search
CPC . A61K 31/70; C07K 1/18; C07K 1/36; C07K 16/065; A01N 25/04; A01N 25/10
See application file for complete search history.

(56) References Cited

U.S. PATENT DOCUMENTS

| | | | |
|---|---|---|---|
| RE30,985 E | 6/1982 | Cartaya | |
| 4,399,216 A | 8/1983 | Axel | |
| 4,560,655 A | 12/1985 | Baker | |
| 4,657,866 A | 4/1987 | Kumar | |
| 4,767,704 A | 8/1988 | Cleveland et al. | |
| 4,816,567 A | 3/1989 | Cabilly et al. | |
| 4,927,762 A | 5/1990 | Darfler | |
| 5,122,469 A | 6/1992 | Mather et al. | |
| 5,591,828 A | 1/1997 | Bosslet et al. | |
| 5,614,405 A * | 3/1997 | Eibl ..................... | A61L 2/0023 435/236 |
| 5,770,199 A | 6/1998 | Eibl et al. | |
| 6,136,321 A | 10/2000 | Barrett et al. | |
| 6,180,401 B1 | 1/2001 | Chen et al. | |
| 2003/0228244 A1 | 12/2003 | Perez | |
| 2006/0276339 A1* | 12/2006 | Windsor ................ | A01N 25/32 504/127 |
| 2007/0111938 A1 | 5/2007 | Pert et al. | |
| 2010/0330071 A1 | 12/2010 | Teschner et al. | |
| 2012/0115204 A1* | 5/2012 | Christensen ......... | C07K 14/745 435/219 |
| 2012/0208982 A1* | 8/2012 | Felgenhauer ........ | C07K 14/755 530/383 |

FOREIGN PATENT DOCUMENTS

| | | |
|---|---|---|
| CN | 103370072 A | 10/2013 |
| EP | 0 117 058 B1 | 8/1984 |
| EP | 0 117 060 A2 | 8/1984 |
| EP | 0 117 060 A3 | 8/1984 |
| EP | 0 307 247 A2 | 3/1989 |
| EP | 0 307 247 A3 | 3/1989 |
| EP | 0 307 247 B1 | 3/1989 |
| EP | 0 404 097 B1 | 12/1990 |
| JP | 2005-502589 A | 1/2005 |
| JP | 2012-523851 A | 10/2012 |
| WO | WO-87/00195 A1 | 1/1987 |
| WO | WO-90/03430 A1 | 4/1990 |
| WO | WO-91/08291 A2 | 6/1991 |
| WO | WO-91/08291 A3 | 6/1991 |
| WO | WO-1993/11161 A1 | 6/1993 |
| WO | WO-1998/53860 A1 | 12/1998 |
| WO | WO-2002/072636 A2 | 9/2002 |
| WO | WO-2002/072636 A3 | 9/2002 |
| WO | WO-2010/123908 A1 | 10/2010 |
| WO | WO2012082931 A1 | 6/2012 |

OTHER PUBLICATIONS

CAS registry list for 9005-65-6, CAS A Division of the American Chemical Society, 2018: pdf pp. 1-4.*
Barnes et al. "Method for Growth of Cultured Cells in Serum-Free Medium," *Anal. Biochem.* 102:255-270, (1980).
ChemIDPlus No. 4292-10-8, located at <https://chem.nlm.nih.gov/chemidplus/rn/4292-10-8>, last visited on Aug. 14, 2017, 4 pages.
ChemIDPlus No. 9005-64-5, located at <https://chem.nlm.nih.gov/chemidplus/number/9005-64-5>, last visited on Aug. 14, 2017, 6 pages.
ChemIDPlus No. 9005-64-6, located at <https://chem.nlm.nih.gov/chemidplus/rn/9005-65-6>, last visited on Aug. 14, 2017, 6 pages.
ChemIDPlus No. 25322-68-3, located at <https://chem.nlm.nih.gov/chemidplus/rn/25322-68-3>, last visited on Aug. 14, 2017, 17 pages.
ChemIDPlus No. 27252-75-1, located at <https://chem.nlm.nih.gov/chemidplus/rn/27252-75-1>, last visited on Aug. 14, 2017, 4 pages.

(Continued)

*Primary Examiner* — Barry A Chestnut
(74) *Attorney, Agent, or Firm* — Morrison & Foerster LLP

(57) ABSTRACT

The invention provides for methods of inactivating virus in product feedstream in a manufacturing process of a therapeutic polypeptide using an environmentally compatible detergent. The environmentally compatible detergent does not adversely affect product quality while effectively inactivating virus in the feedstream.

55 Claims, 6 Drawing Sheets

(56) References Cited

OTHER PUBLICATIONS

ChemIDPlus No. 29836-26-8, located at <https://chem.nlm.nih.gov/chemidplus/rn/29836-26-8>, last visited on Aug. 14, 2017, 4 pages.
ChemIDPlus No. 58846-77-8, <located at https://chem.nlm.nih.gov/chemidplus/rn/58846-77-8>, last visited on Aug. 14, 2017, 3 pages.
ChemIDPlus No. 59122-55-3, located at <https://chem.nlm.nih.gov/chemidplus/rn/59122-55-3>, last visited on Aug. 14, 2017, 3 pages.
ChemIDPlus No. 64366-70-7, located at <https://chem.nlm.nih.gov/chemidplus/rn/64366-70-7>, last visited on Aug. 14, 2017, 3 pages.
ChemIDPlus No. 68439-46-3, located at <https://chem.nlm.nih.gov/chemidplus/rn/68439-46-3>, last visited on Aug. 14, 2017, 4 pages.
ChemIDPlus No. 68515-73-1, located at <https://chem.nlm.nih.gov/chemidplus/rn/68515-73-1>, last visited on Aug. 14, 2017, 4 pages.
ChemIDPlus No. 68937-66-6, located at <https://chem.nlm.nih.gov/chemidplus/rn/68937-66-6>, last visited on Aug. 14, 2017, 3 pages.
ChemIDPlus No. 69227-22-1, <located at https://chem.nlm.nih.gov/chemidplus/rn/69227-22-1>, last visited on Aug. 14, 2017, 3 pages.
ChemIDPlus No. 110615-47-9, <located at https://chem.nlm.nih.gov/chemidplus/rn/110615-47-9>, last visited on Aug. 14, 2017, 3 pages.
ChemIDPlus No. 132778-08-6, located at <https://chem.nlm.nih.gov/chemidplus/rn/132778-08-6>, last visited on Aug. 14, 2017, 3 pages.
ChemIDPlus No. 1226892-43-8, located at <https://chem.nlm.nih.gov/chemidplus/rn/1226892-43-8>, last visited on Aug. 14, 2017, 3 pages.
Clackson et al. "Making Antibody Fragments Using Phage Display Libraries," *Nature* 352:624-628, (Aug. 15, 1991).
Gething et al. "Cell-Surface Expression of Influenza Haemagglutinin From a Cloned DNA Copy of the RNA Gene," *Nature* 293:620-625, (Oct. 22, 1981).
Goodman et al. "Immunoglobulin Proteins," Chapter 6 in *Basic and Clinical Immunology*, 8$^{th}$ edition, Stites, D.P. et al. ed., Appleton & Lange, Norwalk, CT, pp. 71-79, (1994).
Graham et al. "A New Technique for the Assay of Infectivity of Human Adenovirus 5 DNA," *Virology* 52(2):456-456, (Apr. 1973).
Graham et al. "Characteristics of a Human Cell Line Transformed by DNA From Human Adenovirus Type T," *J. Gen. Virol.* 36:59-72, (1977).
Ham et al. "Media and Growth Requirements," Chapter 5 in *Methods of Enzymology*, Academic Press, Inc., vol. 58, pp. 44-93, (1979).
Hammerling et al. "Production of Hybridmoas in the Rodent System," Chapter 12 in *Monoclonal Antibodies and T-Cell Hybridomas*, Elservier, N.Y., pp. 563-681, (1981).
Hawley-Nelson et al. "LipofectAMINE$^{TM}$ Reagent: A New, Higher Efficiency Polycationic Liposome Transfection Reagent," *Focus* 15(3):73, (1993).
Holliger et al. "Diabodies": Small Bivalent and Bispecific Antibody Fragments, *Proc. Natl. Acad. Sci. USA* 90:6444-6448, (Jul. 1993).
Huang et al. "In Vivo Deamidation Characterization of Monoclonal Antibody by LC/MS/MS," *Anal. Chem.* 77(5):1432-1439, (Mar. 1, 2005).
Jones et al. "Replacing the Complementarity Determining Regions in a Human Antibody With Those From a Mouse," *Nature* 321:522-525, (May 29, 1986).
Keown et al. "Methods for Introducing DNA Into Mammalian Cells," Chapter 41 in *Methods in Enzymology*, Academic Press, Inc., vol. 185, pp. 527-537, (1993).
Köhler et al. "Continuous Cultures of Fused Cells Secreting Antibody of Predefined Specificity," *Nature* 256:495-497, (Aug. 7, 1975).
Köhler et al. "Derivation of Specific Antibody-Producing Tissue Culture and Tumor Lines by Cell Fusion," *Eur. J. Immunol.* 6(7):511-519, (Jul. 1976).
Lucena et al. "A New Methodology for Polyvalent Intravenous Immunoglobulin Solution Production With a Two-Stage Process of Viral Inactivation," *BJPS Brazilian Journal of Pharmaceutical Sciences* 46(4):777-783, (2010).

Lyubarskay et al. "Analysis of Recombinant Monoclonal Antibody Isoforms by Electrospray Ionization Mass Spectrometry As a Strategy for Streamlining Characterization off Recombinant Monoclonal Antibody Charge Heterogeneity," *Anal. Bioch.* 384:24-39, (2006, e-pub. Oct. 25, 2005).
Mansour et al. "Disruption of the Proto-Oncogene int-2 in Mouse Embryo-Derived Stem Cells: A General Strategy for Targeting Mutations to Non-Selectable Genes," *Nature* 336:348-352, (Nov. 24, 1988).
Mantei et al. "Rabbit β-Globin mRNA Production in Mouse L Cells Transformed With Cloned•Rabbit β-globin Chromosomal DNA," *Nature* 281:40-46, (Septmeber 6, 1979).
Marks et al. "By-Pass Immunization. Human Antibodies from V-Gene Libraries Displayed on Phage," *J. Mol. Biol.* 222:581-597, (1991).
Mather. "Establishment and Characterization of Two Distinct Mouse Testicular Epithelial Cell Lines," *Biol. Reprod.* 23:243-251, (1980).
Mather et al. "Culture of Testicular Cells in Hormone-Supplemented Serum-Free Medium," *Annals N.Y. Acad. Sci.* 383:44-68, (1982).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Pluckthün. "Antibodies from *Escherichia coli*," *The Pharmacology of Monclonal Antibodies*, Rosenburg et al. eds., Springer-Verlag, New York, vol. 113, pp. 269-315, (1994).
Presta. "Antibody Engineering," *Curr. Op. Struct. Biol.* 2:593-596, (1992).
PubChem CID No. 443314, located at https://pubchem.ncbi.nlm.nih.gov/compound/443314>, last visited on Aug. 14, 2017, 25 pages.
PubChem CID No. 93321, located at <https://pubchem.ncbi.nlm.nih.gov/compound/93321>, last visited on Aug. 14, 2017, 19 pages.
PubChem CID No. 3033856, located at <https://pubchem.ncbi.nlm.nih.gov/compound/3033856>, last visited on Aug. 14, 2017, 20 pages.
OECD. OECD Series on Testing and Assessment, No. 54. Current Approaches in The Statistical Analysis of Ecotoxicity Data: A Guidance to Application, 147 pages, (May 9, 2006).
OECD. "OECD Guidelines for the Testing of Chemicals. Freshwater Alga and Cyanobacteria, Growth Inhibition Test 201," 25 pages, Adopted: 23 Mar. 23, 2006, Annex 5 corrected: Jul. 28, 2011.
OECD. "OECD Guideline for Testing of Chemicals, " *Daphnia* sp., Acute Immobilisation Testand Reproduction Test 202, Adopted by the Council on Apr. 4, 1984, 16 pages.
OECD. "OECD Guideline for Testing of Chemicals. Fish, Acute Toxicity Test 203," Adopted by the Council on Jul. 17, 1992, 9 pages.
OECD. "OECD Guidelines for the Testing of Chemicals. Activated Sludge, Respiration Inhibition Test (Carbon and Ammonium Oxidation) 209," Adopted: Jul. 22, 2010, 18 pages.
OECD. "OECD Guidelines for the Testing of Chemicals. *Daphnia magna* Reproduction Test 211," Adopted: Oct. 2, 2012, 18 pages.
OECD. "OECD Guideline for Testing of Chemicals. Ready Biodegradability 301," Adopted by the Council on Jul. 17, 1992, 62 pages.
Riechmann et al. "Reshaping Human Antibodies for Therapy," *Nature* 332:323-329, (Mar. 24, 1988).
Urlaub et al. "Isolation of Chinese Hamster Cell Mutants Deficient in Dihydrofolate Reductase Activity," *Proc. Natl. Acad. Sci. USA* 77:4216-4220, (Jul. 1980).
Zhang et al. "Unveiling a Glycation Hot Spot in a Recombinant Humanized Monoclonal Antibody," *Analytical Chem.* 80:2379-2390, (2008).
Extended EP SR Report mailed on Jun. 2, 2017, for EP Application No. 14862284.8, filed on , 10 pages.
International Search Report dated Jan. 27, 2015, for PCT Application No. PCT/US14/65391, filed on Nov. 14, 2014, 3 pages.
Written Opinion dated Jan. 27, 2015, for PCT Application No. PCT/US14/65391, filed on Nov. 14, 2014, 4 pages.

\* cited by examiner

METHODS FOR VIRAL INACTIVATION USING ECO-FRIENDLY DETERGENTS

CROSS-REFERENCE TO RELATED APPLICATIONS

This application is a continuation of PCT/US2014/065391, filed Nov. 13, 2014, which claims priority from U.S. Provisional Patent Application No. 61/905,075, filed Nov. 15, 2013, and U.S. Provisional Patent Application No. 61/937,284, filed Feb. 7, 2014, the contents of which are incorporated herein by reference in their entireties.

FIELD OF INVENTION

The invention provides for methods of viral inactivation using detergents.

BACKGROUND OF THE INVENTION

Biotechnological production of pharmaceutical active substances needs ancillary substances for various purposes. Detergents are used at the end of the synthesis phase to lyse the producing cells, to liberate the synthesis products for purification, and as a protection against viral or bacterial contamination. After purification of desired products, growth media and buffers used in product purification are inactivated and drained to the wastewater. Such discharges may cause environmental concern as estimated by environmental risk assessment (ERA) for detergent.

Current protocols for the inactivation of virus in biotechnical production of pharmaceutical active substances often rely on the use of Triton X-100. A degradation product of Triton X-100 is octylphenol, an ecotoxin with demonstrated estrogenic effects. Defined limits for octylphenol discharge is 0.01 to 0.1 ppb. As such, the use of Triton-X in biotechnological processes may require the use of complex and costly means to remove octylphenol from wastestreams. What is needed is an environmentally compatible detergent for use in production of biologics.

All references cited herein, including patent applications and publications, are incorporated by reference in their entirety.

BRIEF SUMMARY OF THE INVENTION

The invention provides methods of inactivating virus in a product feedstream in a manufacturing process of a therapeutic polypeptide, the method comprising the step of subjecting the feedstream to a detergent, wherein the detergent is environmentally compatible. The method maintains product quality of the therapeutic polypeptide; for example, compared to a method using Triton X-100 or a method without detergent.

In some embodiments, the therapeutic polypeptide's product quality results in no more than a 5% change in product variants out of the total polypeptide in the product feedstream. In some embodiments, the product variants do not increase by more than 5% out of the total polypeptide in the product feedstream. In some embodiments, the product variants are size variants, charge variants, oxidation variants, deamidation variants, glycation variants or variants with altered glycan profiles. In some embodiments, the product variants are acidic and/or basic product variants. In some embodiments of the invention, subjecting the feedstream to detergent does not increase fragmentation of the polypeptide by more than about 5%. In some embodiments, subjecting the feedstream to detergent does not increase aggregation in the feedstream by more than about 5%. In other embodiments, subjecting the feedstream to detergent does not reduce the yield of the polypeptide in the manufacturing process by more than about 5%.

The invention provides methods of inactivating virus in a product feedstream in a manufacturing process of a therapeutic polypeptide, the method comprising the step of subjecting the feedstream to a detergent, wherein the environmentally compatible detergent is added to the feedstream to a final concentration of about 0.01% to about 10%. In some embodiments, the detergent is added to the feedstream to a final concentration of about 0.3% to about 1%. In some embodiments, the feedstream is subjected to the detergent for at least about 1 minute to at least about 48 hours. In other embodiments, the feedstream is subjected to the detergent for at least about 15 minutes to at least about 3 hours. In yet other embodiments, the feedstream is subjected to the detergent for at least about 1 hour. In some embodiments of the invention, the feedstream is subjected to the detergent at about 4° C. to about 30° C. In other embodiments, the feedstream is subjected to the detergent at about 15° C. to about 20° C.

In some embodiments of the invention, the detergent is a non-ionic detergent or zwitterionic detergent. In some embodiments, the detergent has a hydrophile lipophile balance (HLB) from about 12 to about 15.

In some embodiments of the invention, the detergent does not comprise or form octylphenol. In some embodiments, the detergent does not comprise or form peroxide.

In some embodiments of the invention, the feedstream comprising the detergent is of low turbidity. In some embodiments, addition of the detergent to the feedstream does not increase the turbidity of the feedstream.

In some embodiments of the invention, upon disposal the detergent's Predicted Environmental Concentration (PEC) in the receiving water body resulting from use of the detergent is below the Predicted No-Effect Concentration (PNEC) of the detergent. In further embodiments, the PEC is lower than the PNEC.

In some embodiments of the invention, the environmentally compatible detergent comprises an alkyl glucoside. In further embodiments, the alkyl glucoside is a decyl glucoside. In other embodiments, the environmentally compatible detergent is an alcohol ethoxylate. In yet other embodiments, the environmentally compatible detergent is an alkyl polyethylene glycol ether. In some embodiments, the environmentally compatible detergent has a CAS registry number of CAS 9005-64-5, CAS 9005-65-6. CAS 126-43-8, 68515-73-1, CAS 58846-77-8, CAS 59122-55-3, CAS 110615-47-9, CAS 29836-26-8, CAS 64366-70-7, CAS 68937-66-6, CAS 69227-22-1, CAS 25322-68-3, CAS 27252-75-1, CAS 4292-10-8, CAS 132778-08-6, CAS 110615-47-9, CAS 68515-73-1, or CAS 68439-46-3.

In some embodiments, the detergent comprises one or more surfactants. In further embodiments, the detergent comprises one or more surfactants, preservatives, and chelating agents.

In some aspects, the invention provides methods of inactivating virus in a product feedstream in a manufacturing process of a therapeutic polypeptide, the method comprising the step of subjecting the feedstream to an environmentally compatible detergent, wherein the feedstream comprises a harvested cell culture fluid. In some embodiments, detergent is added to the harvested cell culture fluid. In other embodiments, the feedstream comprises a capture pool or a recovered product pool. In further embodiments, the capture pool or recovered product pool is an affinity chromatography pool. In yet further embodiments, the capture pool or recovered product pool is a protein A pool, a protein G pool or a protein L pool. In other embodiments, the capture pool or recovered product pool is a mixed mode chromatography pool. In further embodiments, the capture pool is a CaptoAdhere pool.

In some embodiments of the invention, the environmentally compatible detergent is used in combination with an anti-foaming agent. In some embodiments, the antifoaming agent is simethicone.

In some embodiments, the invention provides methods of inactivating virus in a product feedstream in a manufacturing process of a therapeutic polypeptide, the method comprising the step of subjecting the feedstream to an environmentally compatible detergent, wherein the virus is an enveloped virus. In some embodiments, the virus is a retrovirus, a herpesvirus, a flavivirus, a poxvirus, a hepadnavirus, a hepatitis virus, an orthomyxovirus, a paramyxovirus, a rhabdovirus, or a togavirus. In some embodiments, the viral log reduction value (LRV) of the detergent in the feedstream is greater than about one. In further embodiments, the viral LRV is greater than about four. In some embodiments, the LRV is calculated based on infectivity assay. In further embodiments, the infectivity assay is a plaque assay or a TCID$^{50}$ assay.

In some embodiments of the invention, the method further comprises a step of filtering the feedstream after adding the detergent. In some embodiments, the feedstream is filtered at least about 15 minutes to at least about 48 hours after addition of the detergent. In further embodiments, the feedstream is filtered at least about 1 hour to at least about 3 hours after addition of the detergent. In other embodiments, the feedstream is filtered after about 1 hour after addition of the detergent. In some embodiments, the filter is an ultrafilter or a depth filter.

In some embodiments of the invention, the feedstream is subjected to chromatography after addition of the detergent. In some embodiments, the chromatography is one or more of an affinity chromatography, an ion exchange chromatography a hydrophobic interaction chromatography, a hydroxyapatite chromatography, or a mixed mode chromatography. In some embodiments, the affinity chromatography is a protein A chromatography, a protein G chromatography or a protein L chromatography. In other embodiments, the ion exchange chromatography is an anion exchange chromatography or a cation exchange chromatography. In other embodiments, the mixed mode chromatography is a CaptoAdhere chromatography.

In some aspects, the invention provides methods of inactivating virus in a product feedstream in a manufacturing process of a therapeutic polypeptide, the method comprising the step of subjecting the feedstream to an environmentally compatible detergent, wherein the therapeutic polypeptide is an antibody, an immunoadhesin, an enzyme, a growth factor, a receptor, hormone, a regulatory factor, a cytokine, an Fc fusion polypeptide, an antigen, or a binding agent. In further embodiments, the antibody is a monoclonal antibody, a chimeric antibody, a humanized antibody, a human antibody, a bispecific antibody, or an antibody fragment. In some embodiments, the therapeutic polypeptide is produced in mammalian cells. In some embodiments, the mammalian cell line is a Chinese Hamster Ovary (CHO) cells, or baby hamster kidney (BHK) cells, murine hybridoma cells, or murine myeloma cells.

DETAILED DESCRIPTION

Figure 1:
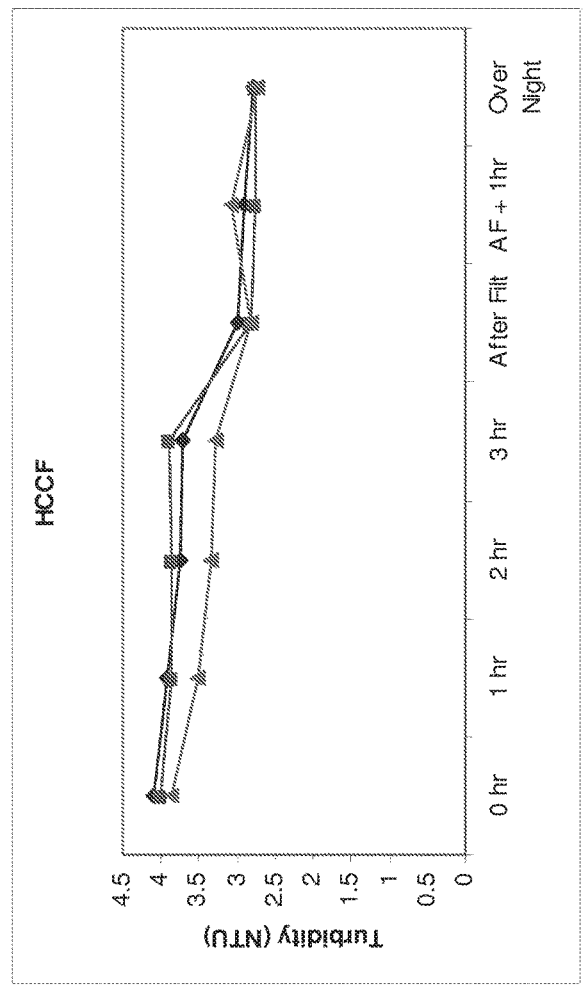
FIG. 1 shows detergent mixing turbidity analysis of the MAb1 HCCF control without detergent using various mixing methods; no mixing (diamonds), stir bar (squares) and overhead agitator (triangles).

The invention provides method of inactivating virus in a product feedstream in a manufacturing process of a therapeutic polypeptide using environmentally compatible (eco-friendly) detergents. The use of environmentally compatible detergents does not adversely affect product quality of the therapeutic polypeptide. For example, the use of environmentally compatible detergents does not result in an increase in product variants such as, but not limited to, size variants including product fragments and aggregates, charge variants including acidic and basic variants, deamination variants, and glycation variants. In some aspects, the use of environmentally compatible detergents does not adversely affect the clearance of process impurities such as CHOP, nucleic acids, leached Protein A, product variants, endotoxin, viral contaminants, cell culture media component, and the like.

I. GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.); *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E.

Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Erperimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. DEFINITIONS

The term "detergent" refers to an agent that may comprise salts of long-chain aliphatic bases or acids, or hydrophilic moieties such as sugars, and that possess both hydrophilic and hydrophobic properties. Having both hydrophilic and hydrophobic properties, the detergent can exert particular effects. As used herein, detergents have the ability to disrupt viral envelopes and inactivate viruses. In some examples, a detergent may be a composition comprising a surfactant and one or more other agents such as chelating agents and preservatives.

A "surfactant" or "surface active agent" is a compound, typically (but not necessarily) an organic compound, that contains both hydrophobic and hydrophilic groups, and is thus semi-soluble in both organic and aqueous solvents. Surfactants can be non-ionic, cationic or anionic.

As used herein, an "environmentally compatible" substance is a substance which causes minimal harmful effects on the environment. For example, an environmentally compatible substance would essentially be nontoxic to animal and/or plant life.

A "predicted environmental concentration" of "PEC" is the predicted concentration of a substance in waste material discharged into the receiving water body in environment. For example, a predicted environmental concentration of a detergent used for viral inactivation in the preparation of a therapeutic protein is the concentration of detergent in the waste stream that is discharged into the environment.

A "predicted no-effect concentration" or "PNEC" is the predicted concentration of a substance in waste material that is safe for discharging to the environment without harmful effects; for example, to the biota of the receiving fresh water and/or marine water.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

An "isolated polypeptide" means a polypeptide that has been recovered from a cell or cell culture from which it was expressed.

The term "polypeptide charge variant" as used herein refers to polypeptide that has been modified from its native state such that the charge of the polypeptide is altered. In some examples, charge variants are more acidic than the parent polypeptide; i.e. have a lower pI than the parent polypeptide. In other examples, charge variants are more basic than the parent polypeptide; i.e. have a higher pI than the parent polypeptide. Such modifications may be engineered or the result of natural processes such as oxidation, deamidation, C-terminal processing of lysine residues, N-terminal pyroglutamate formation, and glycation. In some examples, a polypeptide charge variant is a glycoprotein where the glycan attached to the protein is modified such that the charge of the glycoprotein is altered compared to parent glycoprotein, for example, by addition of sialic acid or its derivatives. An "antibody charge variant" as used herein is an antibody or fragment thereof wherein the antibody or fragment thereof has been modified from its native state such that the charge of the antibody or fragment thereof is altered.

A "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

An "isolated nucleic acid" means and encompasses a non-naturally occurring, recombinant or a naturally occurring sequence outside of or separated from its usual context.

A "purified" polypeptide means that the polypeptide has been increased in purity, such that it exists in a form that is more pure than it exists in its natural environment and/or when initially produced and/or synthesized and/or amplified under laboratory conditions. Purity is a relative term and does not necessarily mean absolute purity.

A "product feedstream" or alternatively, "feedstream" is the material or solution provided for a process purification method which contains a therapeutic polypeptide of interest and which may also contain various impurities. Non-limiting examples may include, for example, harvested cell culture fluid (HCCF), or the collected pool containing the therapeutic polypeptide of interest after one or more purification process steps.

The term "antibody" or "antibodies" is used in the broadest sense and specifically covers, for example, single monoclonal antibodies (including agonist, antagonist, and neutralizing antibodies), antibody compositions with polyepitopic specificity, polyclonal antibodies, single chain antibodies, multispecific antibodies (e.g., bispecific antibodies), immunoadhesins, and fragments of antibodies as long as they exhibit the desired biological or immunological activity. The term "immunoglobulin" (Ig) is used interchangeable with antibody herein.

"Antibody fragments" comprise a portion of a full length antibody, generally the antigen binding or variable region thereof. Examples of antibody fragments include Fab, Fab', F(ab')2, and Fv fragments; single-chain antibody molecules;

diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g., Old World Monkey, Ape etc), and human constant region sequences.

"Humanized" antibodies are forms of non-human (e.g., rodent) antibodies that are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992).

"Impurities" refer to materials that are different from the desired polypeptide product. The impurity includes, without limitation: host cell materials, such as CHOP; leached Protein A; nucleic acid; a variant, size variant, fragment, aggregate or derivative of the desired polypeptide; another polypeptide; endotoxin; viral contaminant; cell culture media component, etc.

"Ultrafiltration" is a form of membrane filtration in which hydrostatic pressure forces a liquid against a semipermeable membrane. Suspended solids and solutes of high molecular weight are retained, while water and low molecular weight solutes pass through the membrane. In some examples, ultrafiltration membranes have pore sizes in the range of 1 to 100 nm. The terms "ultrafiltration membrane" and "ultrafiltration filter" may be used interchangeably.

A "virus retentive filter", "virus filter", "virus membrane", or "virus retentive membrane" is a type of ultrafiltration filter/membrane used for size-based removal of viruses from aqueous solutions containing virus particles. In particular, a virus retentive membrane has a pore size sufficient to retain the virus, while still allowing the desired polypeptide product to pass through.

As used herein, the term "fouling" refers to the accumulation and formation of unwanted materials on the surfaces of processing equipment. Fouling may be characterized as a combined, unsteady state, momentum, mass and heat transfer problem with chemical, solubility, corrosion and biological processes also taking place. Fouling may be due to precipitation, i.e., calcium phosphate precipitation.

As used herein, "adventitious agent" encompasses viruses and bacteria (including bacteria that can pass through sterilization grade filters). An "infectious agent" is a type of "adventitious agent."

It is understood that aspects and embodiments of the invention described herein include "comprising," "consisting," and "consisting essentially of" aspects and embodiments.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

III. METHODS OF THE INVENTION

The invention provides method of inactivating virus in a product feedstream in a manufacturing process of a therapeutic polypeptide using environmentally compatible detergents. The use of environmentally compatible detergents does not adversely affect product quality of the therapeutic polypeptide while effectively inactivating viral contaminants in the feedstream. For example, the use of environmentally compatible detergents does not result in an increase in product variants such as, but not limited to, size variants including product fragments and aggregates, charge variants including acidic and basic variants, deamination variants, and glycation variants.

Typically, the manufacturing process for a therapeutic polypeptide includes expression of the polypeptide in a host cell. In some examples, the host cells are lysed to release the polypeptides. In other examples, the polypeptide is secreted in the media. The harvested cell culture fluid comprising the desired polypeptide may be clarified and subject to one or more chromatographies to purify the desired polypeptide from impurities. Chromatographies may include a flow-through chromatography where the desired product flows through the chromatography and impurities are retained by the chromatography and/or a bind and elute chromatography where the desired product is retained by the chromatography and impurities flow through the chromatography. At some point in the process, the feedstream may be filtered to remove virus. Feedstreams may undergo ultrafiltration and/or diafiltration steps to concentrate the desired polypeptide and to formulate the desired polypeptide into a pharmaceutical formulation. Methods of viral inactivation using an environmentally compatible detergent of the invention may be performed at any step during the manufacturing process. In some embodiments of the invention, virus is inactivated by subjecting the HCCF with an environmentally compatible detergent. In other methods of the invention, virus is inactivated by subjecting a capture pool or a recovered product pool with an environmentally compatible detergent. A capture pool and/or a recovered product pool is the partition of a feedstream comprising the desired product in a separation step in the purification of the product, such as a chromatography, a centrifugation, a filtration and the like. In other methods of the invention, virus is inactivated by subjecting a product feedstream with an environmentally compatible detergent before subjecting the feedstream to a virus filtration step. In other methods of the invention, virus is inactivated by subjecting a product feedstream with an environmentally compatible detergent after subjecting the feedstream to a virus filtration step.

The invention provides method of inactivating virus in a product feedstream in a manufacturing process of a therapeutic polypeptide using environmentally compatible detergents wherein the product quality of the therapeutic polypeptide is maintained during the process while viral contaminants are effectively inactivated. In some embodiments of the invention, treatment of the feedstream in a manufacturing process of a therapeutic polypeptide with an environmentally compatible detergent to inactivate virus in the feedstream does not increase the amount of product variants out of the total protein in the product feedstream in the manufacturing process; for example, compared to the manufacturing process without detergent or with Triton X-100. In some embodiments, the product variants are any one or more of size variants, charge variants, oxidation variants, deamidation variants, glycation variants or variants with altered glycan profiles. In some embodiments of the invention, the product variants are size variants. Size variants include variants where the product is smaller than the desired product; for example, as a result of degradation of the product. In other examples, the size variants are larger than the desired product; for example, as a result of aggregation of the desired product. In some embodiments, product aggregation is the aggregation of two or more product polypeptides in the feedstream. In some embodiments, product aggregation is the aggregation of the product polypeptide with other polypeptides in the feedstream. One skilled in the art can readily measure the formation of size variants. For example, the presence of size variants of the product polypeptide in the feedstream may be determined by size exclusion chromatography, by gel electrophoresis, or by other methods where the size of a polypeptide is readily determined. In some embodiments of the invention, treatment of the feedstream in a manufacturing process of a therapeutic polypeptide with an environmentally compatible detergent to inactivate virus in the feedstream result in more than about 5% changes in product size variants out of the total protein in the product feedstream; for example, compared to the manufacturing process without detergent or with Triton X-100. In some embodiments, the environmentally compatible detergent results in less than about any of 10%, 9%, 8%, 7%, 6%, 5%, 4%, 3%, 2%, 1%, 0.1% increase in product size variants out of the total protein in the product feedstream compared to a manufacturing process without the environmentally compatible detergent; for example, no detergent or Triton X-100.

The invention provides method of inactivating virus in a product feedstream in a manufacturing process of a therapeutic polypeptide using environmentally compatible detergents wherein the product quality of the therapeutic polypeptide is maintained during the process while viral contaminants are effectively inactivated. In some embodiments of the invention, treatment of the feedstream in a manufacturing process of a therapeutic polypeptide with an environmentally compatible detergent to inactivate virus in the feedstream does not increase the amount of product variants in the manufacturing process; for example, compared to the manufacturing process without detergent or with Triton X-100. In some embodiments, the variants are charged variants. Charged variants of the polypeptide may include acidic variants of the polypeptide and basic variants of the parent polypeptide. Examples of acidic variants, i.e. variants with a pI less than the pI of the parent polypeptide, include but are not limited to polypeptides where one or more glutamine and/or asparagine residues have been deamidated. Examples of basic polypeptide variants, i.e. variants with a pI greater than the pI of the parent polypeptide, include but are not limited to variants where an aspartic acid residue has undergone modification to a succinimide moiety. Methods to analyze polypeptides for charge variants are known in the art; for example, by pH-mediated ion exchange chromatography or by isoelectric focusing for charge heterogeneity (e.g., icIEF). In some examples, the product therapeutic polypeptide is subject to one or more chromatographies following addition of detergent prior to analysis of charge variants of the therapeutic polypeptide. For example, an antibody may be subject to an affinity chromatography such as a protein A chromatography following treatment of detergent and prior to charge variant analysis (e.g., pH-mediated ion exchange chromatography). In some embodiments of the invention, treatment of the feedstream in a manufacturing process of a therapeutic polypeptide with an environmentally compatible detergent to inactivate virus in the feedstream result in more than about 5% changes in product variants out of the total protein in the product feedstream; for example, compared to the manufacturing process without detergent or with Triton X-100. In some embodiments, the environmentally compatible detergent results in less than about any of 10%, 9%, 8%, 7%, 6%, 5%, 4%, 3%, 2%, 1%, 0.1% increase in product variants out of the total protein in the product feedstream compared to a manufacturing process without the environmentally compatible detergent; for example, no detergent or Triton X-100.

In some embodiments of the invention, the variants are deamidation variants. As discussed above, a deamidation variant includes polypeptides where one or more glutamine and/or asparagine residues have been deamidated. In some embodiments, deamidation of a product polypeptide results in a change in the charge of the polypeptide. Methods to analyze polypeptides for deamidated variants are known in the art; for example, by pH-mediated ion exchange chromatography or isoelectric focusing. In some examples, the product therapeutic polypeptide is subject to one or more chromatographies following addition of detergent prior to analysis of deamidation variants of the therapeutic polypeptide. For example, an antibody may be subject to an affinity chromatography such as a protein A chromatography following treatment of detergent and prior to deamidation variant analysis (e.g., pH-mediated ion exchange chromatography or isoelectric focusing). In some embodiments of the invention, treatment of the feedstream in a manufacturing process of a therapeutic polypeptide with an environmentally compatible detergent to inactivate virus in the feedstream result in more than about 5% changes in product deamidation variants out of the total protein in the product feedstream; for example, compared to the manufacturing process without detergent or with Triton X-100. In some embodiments, the environmentally compatible detergent results in less than about any of 10%, 9%, 8%, 7%, 6%, 5%, 4%, 3%, 2%, 1%, 0.1% increase in product deamidation variants out of the total protein in the product feedstream compared to a manufacturing process without the environmentally compatible detergent; for example, no detergent or Triton X-100.

In some embodiments of the invention, the variants are oxidation variants. Oxidation variant includes polypeptides where one or more oxygen-reactive amino acid residues, such as methionine, cysteine and tyrosine, have been oxidized. In some embodiments, oxidation of a product polypeptide results in a change in the charge of the polypeptide. Methods to analyze polypeptides for oxidized variants are known in the art. For example, levels of oxidation in a given polypeptide may be determined by LC-mass spectroscopy. In some examples, the product therapeutic polypeptide is subject to one or more chromatographies following addition of detergent prior to analysis of oxidation variants of the therapeutic polypeptide. For example, an antibody may be subject to an affinity chromatography such as a protein A chromatography following treatment of detergent and prior to oxidation variant analysis. In some embodiments of the invention, treatment of the feedstream in a manufacturing process of a therapeutic polypeptide with an environmentally compatible detergent to inactivate virus in the feedstream result in more than about 5% changes in product oxidation variants out of the total protein in the product feedstream; for example, compared to the manufacturing process without detergent or with Triton X-100. In some embodiments, the environmentally compatible detergent results in less than about any of 10%, 9%, 8%, 7%, 6%, 5%, 4%, 3%, 2%, 1%, 0.1% increase in product oxidation variants out of the total protein in the product feedstream compared to a manufacturing process without the environmentally compatible detergent; for example, no detergent or Triton X-100.

In some embodiments of the invention, treatment of the feedstream in a manufacturing process of a therapeutic polypeptide with an environmentally compatible detergent to inactivate virus in the feedstream does not change the glycation of the therapeutic polypeptide product; for example, compared to the manufacturing process without detergent or with Triton X-100. Glycation is a mechanism for generating acidic variants by the formation of various types of covalent adducts, e.g., glycation, where glucose or lactose can react with the primary amine of a lysine residue during manufacturing in glucose-rich culture media or during storage if a reducing sugar is present in the formulation (Lyubarskay Y, et al., (2006) *Anal Biochem.* 348:24-39; Huang L, et al., (2005) *Anal Chem.* 77:1432-1439). Characterization of glycated material can be performed by peptide mapping analysis, liquid chromatography-mass spectrometry (LC-MS) and tandem mass spectrometry (MS/MS) sequencing techniques. In some examples, the product therapeutic polypeptide is subject to one or more chromatographies following addition of detergent prior to the characterization of glycated material. For example, a glycated antibody may be subject to an affinity chromatography such as a protein A chromatography following treatment of detergent and prior to glycation analysis (e.g., LC-MS or MS/MS). In some embodiments, the use of an environmentally compatible detergent for inactivation of virus in a product feedstream in a manufacturing process of a therapeutic polypeptide does not alter the glycation of the therapeutic polypeptide. In some embodiments, the glycation of the parent polypeptide is not altered by more than about 5% compared to a manufacturing process of the therapeutic polypeptide using Triton X-100 or compared to a manufacturing process of the therapeutic polypeptide using no detergent. In some embodiments, the environmentally compatible detergent results in less than about any of 10%, 9%, 8%, 7%, 6%, 5%, 4%, 3%, 2%, 1%, 0.1% change in product glycation compared to a manufacturing process without the environmentally compatible detergent; for example, no detergent or Triton X-100.

In some embodiments of the invention, treatment of the feedstream in a manufacturing process of a therapeutic polypeptide with an environmentally compatible detergent to inactivate virus in the feedstream does not result in changes in glycation pattern of the therapeutic polypeptide product; for example, compared to the manufacturing process without detergent or with Triton X-100. In some embodiments of the invention, the product variants are glycation variants. Glycosylation is a frequently observed post-translational modification where one or more monosaccharide units are linked to a polypeptide. The three major types of glycans are N-linked, O-linked and glycosylphosphatidylinositol. Examples of glycosylated therapeutic polypeptides include monoclonal antibodies where a single conserved N-linked glycosylation site is found an Asn-297 of the Fc chain. The glycan structure at this site plays a role in complement activation and receptor affinity. In some embodiments of the invention, the use of an environmentally compatible detergent for inactivation of virus in a product feedstream in a manufacturing process of a therapeutic polypeptide does not alter the glycation pattern of the therapeutic polypeptide. For example, methods to determine the glycosylation pattern of a polypeptide such as an antibody are known in the art; for example, see the world wide web at chem.agilent.com/Library/applications/5990-9774EN.pdf. In some examples, the product therapeutic polypeptide is subject to one or more chromatographies following addition of detergent prior to the characterization of glycation pattern of the therapeutic polypeptide. For example, a glycated antibody may be subject to an affinity chromatography such as a protein A chromatography following treatment of detergent and prior to glycation analysis (e.g., LC-MS or MS/MS). In some embodiments, the glycation of the therapeutic polypeptide (e.g., an antibody) is not altered by more than about 5% compared to a manufacturing process of the therapeutic polypeptide using Triton X-100 or compared to a manufacturing process of the therapeutic polypeptide using no detergent. In some embodiments, the environmentally compatible detergent results in less than about any of 10%, 9%, 8%, 7%, 6%, 5%, 4%, 3%, 2%, 1%, 0.1% change in product glycation pattern compared to a manufacturing process without the environmentally compatible detergent; for example, no detergent or Triton X-100.

In some embodiments of the invention, treatment of the feedstream in a manufacturing process of a therapeutic polypeptide with an environmentally compatible detergent to inactivate virus in the feedstream does not reduce the product yield during the manufacturing process. For example, treatment of the feedstream with an environmentally compatible detergent does not reduce the product yield of the therapeutic polypeptide in the manufacturing process compared to a manufacturing process of the therapeutic polypeptide using Triton X-100 to inactivate virus or a manufacturing process of the therapeutic polypeptide that does not use a detergent. In some embodiments, the product yield of the therapeutic polypeptide (e.g., an antibody) is not reduced by more than about 5% compared to a manufacturing process of the therapeutic polypeptide using Triton X-100 or compared to a manufacturing process of the therapeutic polypeptide using no detergent. In some embodiments, the environmentally compatible detergent results in less than about any of 10%, 9%, 8%, 7%, 6%, 5%, 4%, 3%, 2%, 1%, 0.1% reduction in product yield compared to a manufacturing process without the environmentally compatible detergent; for example, no detergent or Triton X-100.

In some embodiments of the invention, treatment of the feedstream in a manufacturing process of a therapeutic polypeptide with an environmentally compatible detergent to inactivate virus in the feedstream does not alter the clearance of process impurities during the manufacturing process. For example, treatment of the feedstream with an environmentally compatible detergent does not alter clearance of impurities in the manufacturing process compared to a manufacturing process of the therapeutic polypeptide using Triton X-100 to inactivate virus or a manufacturing process of the therapeutic polypeptide that does not use a detergent. In some embodiments, use of the environmentally compatible detergent does not alter the clearance of process impurities in a particular step in the manufacturing process, such as a chromatography step, a filtration step, a concentration step and the like. In some embodiments, use of the environmentally compatible detergent does not alter the clearance of process impurities in the overall in the manufacturing process of the therapeutic polypeptide. Process impurities include CHOP, nucleic acids, leached protein A, polypeptides other than the desired polypeptide, endotoxin, viral contaminant, cell culture media component, and variants, fragments, aggregates or derivatives of the desired polypeptide.

In some embodiments, the invention provides method of inactivating virus in a product feedstream in a manufacturing process of a therapeutic polypeptide using environmentally compatible detergents, wherein the detergent is added to the feedstream to a final concentration of about 0.01% to about 10%. In some embodiments, the detergent is added to the feedstream to a final concentration of about 0.3% to about 1%. In some embodiments, the detergent is added to the feedstream to a final concentration of about 0.3%. In some embodiments, the detergent is added to the feedstream to a final concentration of more than about 0.1%, 0.2%, 0.3%, 0.4%, 0.5%, 0.6%, 0.7%, 0.8%, 0.9%, 1%, 2%, 03%, 4%, 5%, 6%, 7%, 8%, 9%, or 10%. In some embodiments, the product quality of the therapeutic polypeptide is maintained. In some embodiments, viral contaminants are effectively inactivated by the environmentally compatible detergent.

In some embodiments, the invention provides method of inactivating virus in a product feedstream in a manufacturing process of a therapeutic polypeptide using environmentally compatible detergents, wherein feedstream is subjected to the detergent for about 1 minute to about 48 hours. In some embodiments, the feedstream is subjected to the detergent for about 15 minute to about three hours. In some embodiments, the detergent is added to the feedstream to a final concentration of about 0.3% to about 1%. In some embodiments, the feedstream is subjected to the detergent for about one hour. In some embodiments, the feedstream is subjected to the detergent for more than any of about 1 minute, 5 minutes, 15 minutes, 30 minutes, 45 minutes, 1 hour, 2 hours, 3 hours, 4 hours, 5 hours, 6 hours, 9 hours, 12 hours, 16 hours, 20 hours, 24 hours, 30 hours, 36 hours, 42 hours, or 48 hours. In some embodiments, the feedstream is subjected to the detergent for between about any of 1 minute and 5 minutes, 5 minutes and 15 minutes, 15 minutes and 30 minutes, 30 minutes and 45 minutes, 45 minutes and 1 hour, 1 hour and 2 hours, 2 hours and 3 hours, 3 hours and 4 hours, 4 hours and 5 hours, 5 hours and 6 hours, 6 hours and 9 hours, 9 hours and 12 hours, 12 hours and 16 hours, 16 hours and 20 hours, 20 hours and 24 hours, 24 hours and 30 hours, 30 hours and 36 hours, 36 hours and 42 hours, or 42 hours and 48 hours. In some embodiments, the product quality of the therapeutic polypeptide is maintained. In some embodiments, viral contaminants are effectively inactivated by the environmentally compatible detergent.

In some embodiments, the invention provides method of inactivating virus in a product feedstream in a manufacturing process of a therapeutic polypeptide using environmentally compatible detergents, wherein feedstream is subjected to the detergent at about 4° C. to about 30° C. In some embodiments, the feedstream is subjected to the detergent at about 10° C. to about 25° C. In some embodiments, the feedstream is subjected to the detergent at about 15° C. to about 20° C. In some embodiments, the feedstream is subjected to the detergent at about 20° C. In some embodiments, the feedstream is subjected to the detergent at about ambient temperature. In some embodiments, the feedstream is subjected to the detergent at about 4° C., 5° C., 10° C., 15° C., 20° C., 25° C., or 30° C. In some embodiments, the product quality of the therapeutic polypeptide is maintained. In some embodiments, viral contaminants are effectively inactivated by the environmentally compatible detergent.

In some embodiments, the invention provides method of inactivating virus in a product feedstream in a manufacturing process of a therapeutic polypeptide using environmentally compatible detergents, wherein the feedstream comprising the environmentally compatible detergent is of low turbidity. In some embodiments, the invention provides method of inactivating virus in a product feedstream in a manufacturing process of a therapeutic polypeptide using environmentally compatible detergents, wherein addition of the detergent does not affect the turbidity of the feedstream; for example, compared with a manufacturing process with no detergent or a manufacturing process where Triton X-100 is used to inactivate virus. Methods to determine turbidity of a feedstream are known in the art; for example, using an HP spectrometer with a 1-cm path length cuvette. Turbidity is calculated as the average absorbance from 340-360 nm. In some embodiments, the turbidity of the feedstream is not increased by more than about 5% compared to a manufacturing process of the therapeutic polypeptide using Triton X-100 or compared to a manufacturing process of the therapeutic polypeptide using no detergent. In some embodiments, the environmentally compatible detergent results in less than about any of 10%, 9%, 8%, 7%, 6%, 5%, 4%, 3%, 2%, 1%, 0.1% increased turbidity of the feedstream compared to a manufacturing process without the environmentally compatible detergent; for example, no detergent or Triton X-100.

In some embodiments, the invention provides method of inactivating virus in a product feedstream in a manufacturing process of a therapeutic polypeptide using environmentally compatible detergents, wherein the feedstream is a harvested cell culture fluid. In some embodiments, the feedstream comprises a capture pool or a recovered product pool. In some embodiments, the capture pool or recovered product pool is an affinity chromatography pool. In some embodiments, the capture pool or recovered product pool is a protein A pool, a protein G pool or a protein L pool. In some embodiments, the capture pool or recovered product pool is a mixed mode chromatography pool. In some embodiments, the capture pool is a CaptoAdhere pool.

In some embodiments, the invention provides method of inactivating virus in a product feedstream in a manufacturing process of a therapeutic polypeptide using environmentally compatible detergents, wherein the feedstream is filtered after addition of the environmentally compatible detergent. In some embodiments, the feedstream is filtered at least about 15 minutes to at least about 48 hours after addition of the detergent. In some embodiments, the feedstream is filtered at least about 1 hour to at least about 3 hours after addition of the detergent. In some embodiments, the feedstream is filtered after about 1 hour after addition of the detergent. In some embodiments, the feedstream is filtered after about any one of 15 minutes, 30 minutes, 45 minutes, 1 hour, 2 hours, 3 hours, 4 hours, 5 hours, 6 hours, 12 hours, 18 hours, 20 hours, 24 hours, 30 hours, 36 hours, 42 hours, or 48 hours after addition of the detergent. In some embodiments, the filter is an ultrafilter or a depth filter.

In some embodiments, the invention provides method of inactivating virus in a product feedstream in a manufacturing process of a therapeutic polypeptide using environmentally compatible detergents, wherein the feedstream is subject to chromatography after addition of the detergent. In some embodiments, the chromatography is one or more of one or more of an affinity chromatography, an ion exchange chromatography (e.g., cation exchange and/or anion exchange), a hydrophobic interaction chromatography, a hydroxyapatite chromatography, or a mixed mode chromatography. Examples of affinity chromatography materials include, but are not limited to chromatography materials derivatized with protein A or protein G. Examples of affinity chromatography material include, but are not limited to, Prosep-VA, Prosep-VA Ultra Plus, Protein A sepharose fast flow, Tyopearl Protein A. MAbSelect, MAbSelect SuRe and MAbSelect SuRe LX. In some embodiments of the above, the affinity chromatography material is an affinity chromatography column. In some embodiments of the above, the affinity chromatography material is an affinity chromatography membrane. Examples of anion exchange chromatography materials include, but are not limited to Poros HQ 50, Poros PI 50, Poros D, Mustang Q, Q Sepharose FF, and DEAE Sepharose. Examples of cation exchange materials include, but are not limited to Mustang S, Sartobind S, SO3 Monolith, S Ceramic HyperD, Poros XS, Poros HS50, Poros HS20, SPSFF, SP-Sepharose XL (SPXL), CM Sepharose Fast Flow, Capto S, Fractogel Se HiCap, Fractogel SO3, or Fractogel COO. Examples of HIC chromatography materials include, but are not limited to, Toyopearl hexyl 650, Toyopearl butyl 650, Toyopearl phenyl 650, Toyopearl ether 650, Source, Resource, Sepharose Hi-Trap, Octyl sepharose, phenyl sepharose. Examples of hydroxyapatite chromatography material include but are limited to HA Ultrogel, and CHT hydroxyapatite. Examples of mixed mode chromatography materials include, but are not limited to Capto Adhere, QMA, MEP Hypercel, HEA Hypercel, PPA Hypercel, Capto MMC.

Environmentally Compatible Detergents

The invention provides methods of inactivating virus in a product feedstream in a manufacturing process of a therapeutic polypeptide using environmentally compatible (eco-friendly) detergents. The use of environmentally compatible detergents does not adversely affect product quality of the therapeutic polypeptide. In some embodiments, the detergent is a non-ionic detergent or zwitterionic detergent.

In some embodiments, detergent has a hydrophile lipophile balance (HLB) from about 12 to about 15. In some embodiments, the HLB is any one of about 12 to about 14, about 12 to about 13, about 13 to about 14, about 14 to about 15, about 12, about 13, about 14, or about 15.

In some embodiments, the invention provides methods of inactivating virus in a product feedstream in a manufacturing process of a therapeutic polypeptide using an environmentally compatible detergent in combination with an anti-foaming agent. Anti-foaming agents are known in the art. In some embodiments, the anti-foaming agent is simethicone.

In some embodiments of the invention, the environmentally compatible detergent is an alkyl glucoside. In further embodiments, the alkyl glucoside is a decyl glucoside. In other embodiments, the environmentally compatible detergent is an alcohol ethoxylate. In yet other embodiments, the environmentally compatible detergent is an alkyl polyethylene glycol ether.

In some embodiments, the invention provides methods of inactivating virus in a product feedstream in a manufacturing process of a therapeutic polypeptide using environmentally compatible detergents wherein the environmentally compatible detergent is Tween 20 (CAS registry number of CAS 9005-64-5), Tween 80 (CAS registry number 9005-65-6), TBP (CAS registry number 126-43-8), Decyl polyglucoside (CAS registry number 68515-73-1), decyl β-D glucopyranoside (CAS registry number 58846-77-8), n-decyl β-D glucopyranoside (CAS registry number 59122-55-3), lauryl glucoside (CAS registry number 110615-47-9), n-octyl β-D glucopyranoside (CAS registry number 29836-26-8), EcoSurf EH-6 (CAS registry number 64366-70-7), EcoSurf EH-9 (CAS registry number 64366-70-7), EcoSurf SA-7 or EcoSurf SA-9 (CAS registry number 68937-66-6, CAS registry number 69227-22-1, CAS registry number 25322-68-3). Natsurf 265 (CAS registry number 27252-75-1), Lubrizol (CAS registry number 4292-10-8), APG 325N (CAS registry number 132778-08-6). Mackol DG (CAS registry number 110615-47-9), Triton CG 110 (CAS registry number 68515-73-1), or Tomodol 900 (CAS registry number 68439-46-3).

Methods to determine whether a detergent is environmentally compatible under the conditions of the manufacturing processes of the invention are known in the art. For example, the Organisation for Economic Co-operation and Development provides guidelines for testing chemical safety. These guidelines can be found, for example, on the world wide web at oecd.org/chemicalsafety/testing/oecdguidelinesforthetestingofchemicals.htm. Examples of these guidelines are outlined below.

*Daphnia magna* Reproduction Test-OECD 211

The primary objective of the test is to assess the effect of chemicals on the reproductive output of *Daphnia magna*. To this end, young female *Daphnia* (the parent animals), aged less than 24 hours at the start of the test, are exposed to the test substance added to water at a range of concentrations.

The test duration is 21 days. At the end of the test, the total number of living offspring produced is assessed. Reproductive output of the parent animals can be expressed in other ways (e.g., number of living offspring produced per animal per day from the first day offspring were observed) but these should be reported in addition to the total number of living offspring produced at the end of the test. Because of the particular design of the semi-static test compared to other OECD invertebrate reproduction Test Guidelines, it is also possible to count the number of living offspring produced by each individual parent animal. This enables that, contrary to other OECD invertebrate reproduction tests, if the parent animal dies accidentally and/or inadvertently during the test period, its offspring production can be excluded from data assessment. Hence, if parental mortality occurs in exposed replicates, it should be considered whether or not the mortality follows a concentration-response pattern, e.g., if there is a significant regression of the response versus concentration of the test substance with a positive slope (a statistical test like the Cochran-Armitage trend test may be used for this). If the mortality does not follow a concentration-response pattern, then those replicates with parental mortality should be excluded from the analysis of the test result. If the mortality follows a concentration-response pattern, the parental mortality should be assigned as an effect of the test substance and the replicates should not be excluded from the analysis. If the parent animal dies during the test i.e. accidentally from mishandling or accident, or inadvertently due to unexplained incident not related to the effect of the test substance or turns out to be male, then the replicate is excluded from the analysis. The toxic effect of the test substance on reproductive output is expressed as ECx by fitting the data to an appropriate model by non-linear regression to estimate the concentration that would cause x % reduction in reproductive output, respectively, or alternatively as the NOEC/LOEC value (OECD 2006, Environmental Health and Safety Publications, Series on Testing and Assessment Number 54. OECD, Paris). The test concentrations should preferably bracket the lowest of the used effect concentrations (e.g., $EC_{10}$) which means that this value is calculated by interpolation and not extrapolation.

Freshwater Alga and Cyanobacteria, Growth Inhibition Test-OECD 201

The purpose of this test is to determine the effects of a substance on the growth of freshwater microalgae and/or cyanobacteria. Exponentially growing test organisms are exposed to the test substance in batch cultures over a period of normally 72 hours. In spite of the relatively brief test duration, effects over several generations can be assessed.

The system response is the reduction of growth in a series of algal cultures (test units) exposed to various concentrations of a test substance. The response is evaluated as a function of the exposure concentration in comparison with the average growth of replicate, unexposed control cultures. For full expression of the system response to toxic effects (optimal sensitivity), the cultures are allowed unrestricted exponential growth under nutrient sufficient conditions and continuous light for a sufficient period of time to measure reduction of the specific growth rate.

Growth and growth inhibition are quantified from measurements of the algal biomass as a function of time. Algal biomass is defined as the dry weight per volume, e.g., mg algae/litre test solution. However, dry weight is difficult to measure and therefore surrogate parameters are used. Of these surrogates, cell counts are most often used. Other surrogate parameters include cell volume, fluorescence, optical density, etc. A conversion factor between the measured surrogate parameter and biomass should be known.

The test endpoint is inhibition of growth, expressed as the logarithmic increase in biomass (average specific growth rate) during the exposure period. From the average specific growth rates recorded in a series of test solutions, the concentration bringing about a specified x % inhibition of growth rate (e.g., 50%) is determined and expressed as the $E_rC_x$ (e.g., $E_rC_{50}$).

An additional response variable used in this Guideline is yield, which may be needed to fulfil specific regulatory requirements in some countries. It is defined as the biomass at the end of the exposure period minus the biomass at the start of the exposure period. From the yield recorded in a series of test solutions, the concentration bringing about a specified x % inhibition of yield (e.g., 50%) is calculated and expressed as the EyCx (e.g., EyC50).

In addition, the lowest observed effect concentration (LOEC) and the no observed effect concentration (NOEC) may be statistically determined.

Daphnia sp., Acute Immobilization Assay-OECD 202

Young daphnids, aged less than 24 hours at the start of the test, are exposed to the test substance at a range of concentrations for a period of 48 hours. Immobilisation is recorded at 24 hours and 48 hours and compared with control values. The results are analysed in order to calculate the $EC_{50}$ at 48 h. Determination of the $EC_{50}$ at 24 h is optional.

Fish, Acute Toxicity Test-OECD 203

Fish are exposed to a test substance preferable for a period of 96 hours. Mortalities are recorded at 24, 48, 72 and 96 hours.

Activated Sludge, Respiration Inhibition Test (Carbon and Ammonium Oxidation)-OECD 209

The respiration rates of samples of activated sludge fed with synthetic sewage are measured in an enclosed cell containing an oxygen electrode after a contact time of 3 hours. Under consideration of the realistic exposure scenario, longer contact times could be appropriate. If the test substance is rapidly degraded e.g., abiotically via hydrolysis, or is volatile and the concentration cannot be adequately maintained, additionally a shorter exposure period e.g., 30 minutes can be used. The sensitivity of each batch of activated sludge should be checked with a suitable reference substance on the day of exposure. The test is typically used to determine the $EC_x$ (e.g., $EC_{50}$) of the test substance and/or the no-observed effect concentration (NOEC).

The inhibition of oxygen uptake by micro-organisms oxidizing organic carbon may be separately expressed from that by micro-organisms oxidizing ammonium by measurement of the rates of uptake of oxygen in the absence and presence of N-allylthiourea, a specific inhibitor of the oxidation of ammonium to nitrite by the first-stage nitrifying bacteria. In this case the percentage inhibition of the rate of oxygen uptake is calculated by comparison of the rate of oxygen uptake in the presence of a test substance with the mean oxygen uptake rate of the corresponding controls containing no test substance, both in the presence and absence of the specific inhibitor. N-allylthiourea.

Any oxygen uptake arising from abiotic processes may be detected by determining the rate in mixtures of test substance, synthetic sewage medium and water, omitting activated sludge.

Ready Biodegradability-OECD 301

A solution, or suspension, of the test substance in a mineral medium is inoculated and incubated under aerobic conditions in the dark or in diffuse light. The amount of DOC in the test solution due to the inoculum should be kept as low as possible compared with the amount of organic carbon due to the test substance. Allowance is made for the endogenous activity of the inoculum by running parallel blanks with inoculum but without test substance, although the endogenous activity of cells in the presence of a chemical will not exactly match that in the endogenous control. A reference compound is run in parallel to check the operation of the procedures.

In general, degradation is followed by the determination of parameters such as DOC, $CO_2$ production and oxygen uptake and measurements are taken at sufficiently frequent intervals to allow the identification of the beginning and end of biodegradation. With automatic respirometers the measurement is continuous. DOC is sometimes measured in addition to another parameter but this is usually done only at the beginning and end of the test. Specific chemical analysis can also be used to assess primary degradation of the test substance and to determine the concentration of any intermediate substances formed.

Normally, the test lasts for 28 days. Tests however may be ended before 28 days, i.e. as soon as the biodegradation curve has reached a plateau for at least three determinations. Tests may also be prolonged beyond 28 days when the curve shows that biodegradation has started but that the plateau has not been reached by day 28, but in such cases the chemical would not be classed as readily biodegradable.

In some embodiments, the invention provides methods of inactivating virus in a product feedstream in a manufacturing process of a therapeutic polypeptide using environmentally compatible detergents wherein the detergent does not comprise or form peroxide. Methods of determining the peroxide content of a detergent are known in the art. For example, EMD Millipore colorimetric peroxide test can be used to determine the peroxide level of a detergent. In some embodiments of the invention, the a detergent is free of peroxide if the level of peroxide in the detergent is less than about any of 0.5 ppm, 0.4 ppm, 0.3 ppm, 0.2 ppm, or 0.1 ppm.

In some embodiments, the invention provides methods of inactivating virus in a product feedstream in a manufacturing process of a therapeutic polypeptide using environmentally compatible detergents wherein the detergent does not comprise or form octylphenol. Octylphenol may be a degradation product of Triton X-100. In some embodiments of the invention, the feedstream to be discharged into a waste water system comprises octylphenol at a concentration less that about any of 0.1 µg/L, 0.09 µg/L, 0.08 µg/L, 0.07 µg/L, 0.06 µg/L, 0.05 µg/L, 0.04 µg/L, 0.03 µg/L, 0.02 µg/L, and 0.01 µg/L. One skilled in the art would recognize that the environmental impact of a detergent for a waste water system may differ in the waste is discharged into fresh water or marine water. For example, in some embodiments, the feedstream to be discharged into a waste water system comprises octylphenol at a concentration less that about of 0.1 µg/L for a fresh water discharge and less than about 0.01 µg/L for a marine water discharge.

In some embodiments of the invention the predicted environmental concentration (PEC) of detergent in the wastestream following the manufacturing process of the therapeutic polypeptide is the predicted concentration of a detergent in waste material discharged into the receiving water body in environment. In some embodiments of the invention, the predicted no-effect concentration (PNEC) is the predicted concentration of a detergent in waste material that is safe for discharging to the environment without harmful effects; for example, to the biota of the receiving fresh water and/or marine water. In some embodiments of the invention, the PEC is less than the PNEC. In some embodiments of the invention, the PEC is greater than any one of about 0.5-fold, 1-fold, 2-fold, 3-fold, 4-fold, 5-fold, 6-fold, 7-fold, 8-fold, 9-fold, 10-fold, 20-fold, 30-fold, 40 fold, 50-fold, or 100-fold the PNEC.

In some embodiments of the invention, the environmentally compatible detergent comprises a surfactant and one or more additional components. In some embodiments, the detergent comprises a surfactant and one or more chelating agents and/or preservatives. In some embodiments, the chelating agent is ethylenediaminetetraacetic acid (EDTA).

Inactivation of Virus

The invention provides methods for inactivating virus in a product feedstream comprising subjecting the feedstream to an environmentally compatible detergent. The virus may be any virus detailed herein (e.g., an enveloped virus) and the feedstream may be any feedstream detailed herein, such as harvested cell culture fluid (HCCF), a capture pool, or a recovered product pool. The virus inactivated in the feedstream may be any virus that is industrially relevant for manufacturing of products (e.g., polypeptides, cells, tissues). Industrially relevant viruses are known to those of skill in the art. Non-limiting examples of an industrially relevant virus include a retrovirus, a herpesvirus, a flavivirus, a poxvirus, a hepadnavirus, a hepatitis virus, an orthomyxovirus, a paramyxovirus, a rhabdovirus, or a togavirus. In any variation of the invention, a virus is selected from the group consisting of an adenovirus, African swine fever-line virus, arenavirus, arterivirus, astrovirus, baculovirus, badnavirus, barnavirus, birnavirus, bromovirus, bunyavirus, calicivirus, capillovirus, carlavirus, caulimovirus, circovirus, closterovirus, comovirus, coronavirus, cotricovirus, cystovirus, deltavirus, dianthovirus, enamovirus, filovirus, flavivirus, furovirus, fusellovirus, geminivirus, hepadnavirus, herpesvirus, hordeivirus, hypovirus, ideaovirus, inovirus, iridovirus, levivirus, lipothrixvirus, luteovirus, machlomovirus, marafivovirus, microvirus, myovirus, necrovirus, nodavirus, orthomyxovirus, papovavirus, paramyxovirus, partitivirus, parvovirus, phycodnavirus, picornavirus, plamavirus, podovirus, polydnavirus, potexvirus, potyvirus, poxvirus, reovirus, retrovirus, rhabdovirus, rhizidiovirus, sequevirus, siphovirus, sobemovirus, tectivirus, tenuivirus, tetravirus, tobamavirus, tobravirus, togavirus, tombusvirus, totivirus, trichovirus, tymovirus, and umbravirus. In a variation, the invention provides methods for inactivating a subviral agent in a feedstream comprising subjecting the feedstream to an environmentally compatible detergent. In some aspects, the subviral agent is a viroid or a satellite. In another variation, the invention provides methods for inactivating a virus-like agent in a feedstream comprising subjecting the feedstream to an environmentally compatible detergent.

Inactivation of virus in a feedstream can be measured using methods known in the art. In some embodiments of the invention, viral inactivation is expressed as log reduction value (LRV). LRV were calculated as:

$$LRV = \log_{10} \times (\text{total virus in feedstream following treatment with detergent/total virus feedstream before treatment with detergent}).$$

In some embodiments of the invention, the LRV of the environmentally compatible detergent in the feedstream is greater than about 1. In some embodiments of the invention, the LRV of the environmentally compatible detergent in the feedstream is greater than about 4. In some embodiments of the invention, the LRV of the environmentally compatible detergent in the feedstream is greater than about any one of 1, 2, 3, 4, 5, 6. In some embodiments of the invention, the LRV of the environmentally compatible detergent in the feedstream is between about any one of a and 2, 1 and 3, 1 and 4, 1 and 5, 1 and 6, 2 and 3, 2 and 4, 2 and 5, 3 and 4, 3 and 5, 3 and 6, 4 and 5, 4 and 6, or 5 and 6.

Methods to measure virus activity are known in the art. Examples include, but are not limited to TCID50 assays (i.e. determination of the median tissue culture infective dose that will produce pathological change in 50% of cell cultures inoculated) and plaque assays. Other known methods may include, for example, transformation assay, which can be used to determine the titers of the biological activity of non-plaque forming viruses that have the ability to cause cellular growth transformation; or the fluorescent-focus assay which relies on the use of antibody staining methods to detect virus antigens within infected cells in the monolayer, or the endpoint dilution assay which can be used to determine the titers of many viruses, including viruses which do not infect monolayer cells (as an alternative to plaque assays); or viral enzyme assays in which virally-encoded enzymes such as reverse transcriptases or viral proteases are measured.

Polypeptides of Invention

The polypeptides produced by the manufacturing processes and methods detailed herein and present in the compositions provided herein may be homologous to the host cell used to produce the polypeptide, or preferably, may be exogenous, meaning that they are heterologous, i.e., foreign, to the host cell being utilized, such as a human protein produced by a Chinese hamster ovary cell, or a yeast polypeptide produced by a mammalian cell. In some embodiments, the mammalian cell line is a Chinese Hamster Ovary (CHO) cells, or baby hamster kidney (BHK) cells, murine hybridoma cells, or murine myeloma cells. In one variation, the polypeptide is a mammalian polypeptide (such as an antibody) directly secreted into the medium by the host cell. In another variation, the polypeptide is released into the medium by lysis of a cell comprising an isolated nucleic acid encoding the polypeptide.

Any polypeptide that is expressible in a host cell may be produced in accordance with the present disclosure and may be present in the compositions provided. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, cytokine, Fc fusion polypeptide, antigen, immunoadhesin, etc.

Various polypeptides may be produced according to the methods provided herein, and present in the compositions provided herein. Examples of bacterial polypeptides include, e.g., alkaline phosphatase and β-lactamase. Examples of mammalian polypeptides include molecules such as renin, a growth hormone, including human growth hormone; bovine growth hormone; growth hormone releasing factor, parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor, anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase: inhibin: activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-alpha and TGF-beta, including TGF-.beta. 1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors: immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase: T-cell receptors; surface membrane proteins; decay accelerating factor, viral antigen such as, for example, a portion of the AIDS envelope; transport proteins; homing receptors; addressing; regulatory proteins; antibodies; and fragments of any of the above-listed polypeptides.

The feedstock will contain at least one protein, which in one embodiment is an antibody. The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.). Appleton & Lange. Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses; IgG1, IgG2, IgG3, IgG4, IgA1, and IgA2.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Antibody Engineering, 2nd edition (C. Borrebaeck, ed., Oxford University Press, 1995.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).Abs, etc.

Methods for Producing Polypeptides

Cells

The methods and compositions provided may employ any cell that is suitable for growth and/or production of a polypeptide (e.g., an antibody) in a medium described herein, including animal, yeast or insect cells. In one aspect, a cell of the methods and compositions is any mammalian cell or cell type suitable to cell culture and to expression of polypeptides. The methods provided herein (e.g., methods of inactivating virus in cell culture media) and compositions may therefore employ any suitable type of cell, including an animal cell. In one aspect, the methods and compositions employ a mammalian cell. The methods and compositions may also employ hybridoma cells. In one variation, the mammalian cell is a non-hybridoma mammalian cell, which has been transformed with exogenous isolated nucleic acid encoding a desired polypeptide, such as an antibody, antibody fragment (including a ligand-binding fragment), and chimeric antibodies. In one variation, the methods and compositions employ mammalian cells selected from the group consisting of human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK. ATCC CCL 10); Chinese hamster ovary cells/-DHFR (CHO, Urlaub and Chasin, Proc. Natl. Acad. Sci. USA, 77:4216 (1980)); mouse sertoli cells (TM4, Mather. Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In a particular variation, the methods and compositions employ CHO cells. In a particular variation, the culturing of CHO cell lines and expression of polypeptides (e.g., antibodies) from CHO cell lines is employed. The polypeptides (e.g., antibodies) may be secreted into the medium disclosed herein from which the polypeptides may be isolated and/or purified or the polypeptide may be released into the medium disclosed herein by lysis of a cell comprising an isolated nucleic acid encoding the polypeptide.

Methods, vectors, and host cells suitable for adaptation to the synthesis of the polypeptide of interest in recombinant vertebrate cell culture are known in the art and are described, for example, in Gething et al., *Nature,* 293:620-625 (1981); Mantei et al., *Nature,* 281:40-46 (1979); Levinson et al.; EP 117,060; and EP 117,058. A particularly useful plasmid for mammalian cell culture expression of the polypeptide is pRK5 (EP pub. no. 307,247) or pSVI6B (PCT pub. no. WO 91/08291 published Jun. 13, 1991).

Host cells are transformed with expression or cloning vectors and cultured in nutrient media modified as appropriate for inducing promoters, selecting transformants, or amplifying the genes encoding the desired sequences. For mammalian cells, the calcium phosphate precipitation method of Graham and van der Erb, *Virology,* 52:456-457 (1978) or the Lipofectamine™ (Gibco BRL) Method of Hawley-Nelson, *Focus* 15:73 (1193) are preferred. General aspects of mammalian cell host system transformations are known in the art and have been described, for example, by Axel in U.S. Pat. No. 4,399,216 issued Aug. 16, 1983. For various techniques for transforming mammalian cells, see e.g., Keown et al., *Methods in Enzymology* (1989), Keown et al., *Methods in Enzymology,* 185:527-537 (1990), and Mansour et al., *Nature,* 336:348-352 (1988).

The methods and compositions also embrace the use of hybridomas which secrete monoclonal antibodies in cell culture. Monoclonal antibodies are prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, Eur. J. Immunol., 6:511 (1976), and also described by Hammerling et al., In: Monoclonal Antibodies and T-Cell Hybridomas, Elsevier, N.Y., pp. 563-681 (1981) has been widely applied to produce hybrid cell lines that secrete high levels of monoclonal antibodies against many specific antigens.

Polypeptides

The polypeptides produced by the compositions (e.g., cells) and methods detailed herein and present in the compositions provided herein may be homologous to the host cell, or preferably, may be exogenous, meaning that they are heterologous, i.e., foreign, to the host cell being utilized, such as a human protein produced by a Chinese hamster ovary cell, or a yeast polypeptide produced by a mammalian cell. In one variation, the polypeptide is a mammalian polypeptide (such as an antibody) directly secreted into the medium by the host cell. In another variation, the polypeptide is released into the medium by lysis of a cell comprising an isolated nucleic acid encoding the polypeptide.

In one variation, the polypeptide is a sequence of amino acids for which the chain length is sufficient to produce the higher levels of tertiary and/or quaternary structure. In one aspect, the polypeptide will have a molecular weight of at least about 5-20 kD, alternatively at least about 15-20 kD, preferably at least about 20 kD.

Any polypeptide that is expressible in a host cell may be produced in accordance with the present disclosure and may be present in the compositions provided. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. Examples of polypeptides of the invention are described above.

For example, the present invention may be employed to express any pharmaceutically or commercially relevant enzyme, receptor, antibody, hormone, regulatory factor, antigen, binding agent, etc.

Cell Growth and Polypeptide Production

Generally the cells are combined (contacted) with any of the cell culture media described herein under one or more conditions that promote any of cell growth, maintenance and/or polypeptide production. Methods of growing a cell and producing a polypeptide employ a culturing vessel (bioreactor) to contain the cell and cell culture medium. The culturing vessel can be composed of any material that is suitable for culturing cells, including glass, plastic or metal. Typically, the culturing vessel will be at least 1 liter and may be 10, 100, 250, 500, 1000, 2500, 5000, 8000, 10,000 liters or more. Culturing conditions that may be adjusted during the culturing process include but are not limited to pH and temperature.

A cell culture is generally maintained in the initial growth phase under conditions conducive to the survival, growth and viability (maintenance) of the cell culture. The precise conditions will vary depending on the cell type, the organism from which the cell was derived, and the nature and character of the expressed polypeptide.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time. In one variation, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

An initial culturing step is a growth phase, wherein batch cell culture conditions are modified to enhance growth of recombinant cells, to produce a seed train. The growth phase generally refers to the period of exponential growth where cells are generally rapidly dividing, e.g., growing. During this phase, cells are cultured for a period of time, usually 1 to 4 days, e.g., 1, 2, 3, or 4 days, and under such conditions that cell growth is optimal. The determination of the growth cycle for the host cell can be determined for the particular host cell by methods known to those skilled in the art.

In the growth phase, the basal culture medium and cells may be supplied to the culturing vessel in batch. The culture medium in one aspect contains less than about 5% or less than 1% or less than 0.1% serum and other animal-derived proteins. However, serum and animal-derived proteins can be used if desired. In a particular variation, the basal medium has a pH of between about pH 5.0 to about pH 6.9 during HTST treatment to inactivate virus. In one aspect, the pH of the basal medium is lowered to between about pH 5.0 to about pH 6.9 during HTST treatment to inactivate virus prior to the polypeptide production phase of cell culture. In a further aspect, the pH of the media is then brought to between about pH 6.9 to about pH 7.2 for the polypeptide production phase of cell culture. In a further aspect, the pH of the media is then brought to between about pH 6.9 to about pH 7.2 after HTST treatment for the polypeptide production phase of cell culture. In another particular variation, the basal media comprises limiting the total amount of phosphate and calcium to less than about 10 mM during HTST treatment to inactivate virus. In one aspect, the total amount of phosphate and calcium in the media is limited to less than about 10 mM during HTST treatment to inactivate virus prior to the polypeptide production phase of cell culture. In a further aspect, the total amount of phosphate and calcium in the media is then raised to a level sufficient for the polypeptide production during the polypeptide production phase of cell culture. In another variation, the basal medium has a pH of between about pH 5.0 to about pH 6.9 and a total amount of phosphate and calcium to less than about 10 mM during HTST treatment to inactivate virus. In one aspect, the pH of the basal medium is lowered to between about pH 5.0 to about pH 6.9 and comprises a total amount of phosphate and calcium to less than about 10 mM during HTST treatment to inactivate virus prior to the polypeptide production phase of cell culture. In a further aspect, the pH of the media is then brought to between about pH 6.9 to about pH 7.2 and the total amount of phosphate and calcium in the media is raised to a level sufficient for the polypeptide production during the polypeptide production phase of cell culture. In any of the aspects, the basal medium is a chemically defined medium. In any of the aspects, the basal medium is a chemically undefined medium. Amino acids, vitamins, trace elements and other media components at one or two times the ranges specified in European Patent EP 307,247 or U.S. Pat. No. 6,180,401 may be used, which documents are herein incorporated by reference in their entireties.

Alternatively, commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the animal cells and may be supplemented with chemically defined media constituents as detailed herein (e.g., by use of a kit as provided). In addition, any of the media described in Ham and Wallace, *Meth. Enz.*, 58:44 (1979), Barnes and Sato, *Anal. Biochem.*, 102:255 (1980), U.S. Pat. Nos. 4,767,704; 4,657,866; 4,927,762; or 4,560,655; WO 90/03430: WO 87/00195; U.S. Pat. No. Re. 30,985; or U.S. Pat. No. 5,122,469, the disclosures of all of which are incorporated herein by reference in their entirety, may be used as culture media for the host cells, each of which may be supplemented with chemically defined media constituents as detailed herein (e.g., by use of a kit as provided).

Any media provided herein may also be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), trace metals (such as iron and copper), and glucose or an equivalent energy source. Any other necessary supplements may also be included at appropriate concentrations that would be known to those skilled in the art.

At a particular point in their growth, the cells may form an inoculum to inoculate a culture medium at the start of culturing in the production phase. Alternatively, the production phase may be continuous with the growth phase. The cell growth phase is generally followed by a polypeptide production phase.

During the polypeptide production phase, the cell culture may be maintained under a second set of culture conditions (as compared to the growth phase) conducive to the survival and viability of the cell culture and appropriate for expression of the desired polypeptide. For example, during the subsequent production phase, CHO cells express recombinant polypeptides and proteins well within a range of 25° C. to 35° C. Multiple discrete temperature shifts may be employed to increase cell density or viability or to increase expression of the recombinant polypeptide or protein. As used herein, the term "polypeptide production phase" or "protein expression phase" can refer to the cell culture phase wherein the cell culture produces a biologic drug product (e.g., a polypeptide).

The cells may be maintained in the subsequent production phase until a desired cell density or production titer is reached. In one embodiment, the cells are maintained in the subsequent production phase until the titer to the recombinant polypeptide reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture.

In certain cases, it may be beneficial or necessary to supplement the cell culture during the subsequent polypeptide production phase with nutrients or other medium components that have been depleted or metabolized by the cells. For example, it might be advantageous to supplement the cell culture with nutrients or other medium components observed to have been depleted during monitoring of the cell culture. In some aspects, the one or more depleted components include calcium, phosphate, iron, and copper prior to the subsequent production phase. In some aspects, supplemented media components include calcium, phosphate, iron, and copper. Alternatively or additionally, it may be beneficial or necessary to supplement the cell culture prior to the subsequent polypeptide production phase. In some aspects, the cell culture is supplemented with one or more media components including calcium, phosphate, iron, and copper prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), trace metals (such as iron and copper), amino acids, lipids, or glucose or other energy source. As used herein, the term "feed medium" or "production medium" refers to a cell culture medium used during the polypeptide production phase of cell culture.

IV. EXEMPLARY EMBODIMENTS

1. A method of inactivating virus in a product feedstream in a manufacturing process of a therapeutic polypeptide, the method comprising the step of subjecting the feedstream to a detergent, wherein the detergent is environmentally compatible.

2. The method of embodiment 1, wherein the method maintains product quality of the therapeutic polypeptide compared to a method using Triton X-100 or a method without detergent.

3. The method of embodiment 2, wherein the therapeutic polypeptide's product quality results in no more than a 5% change in product variants out of the total polypeptide in the product feedstream.

4. The method of embodiment 3, wherein the product variants do not increase by more than 5% out of the total polypeptide in the product feedstream.

5. The method of embodiment 3 or 4, wherein the product variants are size variants, charge variants, oxidation variants, deamidation variants, glycation variants or variants with altered glycan profiles.

6. The method of any one of embodiments 3 to 5, wherein the product variants are acidic and/or basic product variants.

7. The method of any one of embodiments 1-6, wherein subjecting the feedstream to detergent does not increase fragmentation of the polypeptide by more than about 5%. This can be measured by size exclusion chromatography (SEC).

8. The method of any one of embodiments 1-7, wherein subjecting the feedstream to detergent does not increase aggregation in the feedstream by more than about 5%. This can be measured by SEC.

9. The method of any one of embodiments 1-8, wherein subjecting the feedstream to detergent does not reduce the yield of the polypeptide in the manufacturing process by more than about 5%. This can be measured by SEC.

10. The method of any one of embodiments 1-9, wherein the detergent is added to the feedstream to a final concentration of about 0.01% to about 10%.

11. The method of any one of embodiments 1-10, wherein the detergent is added to the feedstream to a final concentration of about 0.3% to about 1%.

12. The method of any one of embodiments 1-11, wherein the feedstream is subjected to the detergent for at least about 1 minute to at least about 48 hours.

13. The method of any one of embodiments 1-12, wherein the feedstream is subjected to the detergent for at least about 15 minutes to at least about 3 hours.

14. The method of any one of embodiments 1-13, wherein the feedstream is subjected to the detergent for at least about 1 hour.

15. The method of any one of embodiments 1-14, wherein the feedstream is subjected to the detergent at about 4° C. to about 30° C.

16. The method of any one of embodiments 1-15, wherein the feedstream is subjected to the detergent at about 15° C. to about 20° C.

17. The method of any one of embodiments 1-16, wherein the detergent is a non-ionic detergent or zwitterionic detergent.

18. The method of any one of embodiments 1-17, wherein the detergent has a hydrophile lipophile balance (HLB) from about 12 to about 15.

19. The method of any one of embodiments 1-18, wherein the detergent does not comprise or form octylphenol.

20. The method of any one of embodiments 1-19, wherein the detergent does not comprise or form peroxide.

21. The method of any one of embodiments 1-20, wherein the feedstream comprising the detergent is of low turbidity. This can be measured by an average absorbance from 340-360 nm.

22. The method of any one of embodiments 1-21, wherein addition of the detergent to the feedstream does not increase the turbidity of the feedstream. This can be measured by an average absorbance from 340-360 nm.

23. The method of any one of embodiments 1-22, wherein upon disposal the detergent's Predicted Environmental Concentration (PEC) in the receiving water body resulting from use of the detergent is below the Predicted No-Effect Concentration (PNEC) of the detergent.

24. The method of embodiment 23, wherein the PEC is lower than the PNEC.

25. The method of any one of embodiments 1-24, wherein the environmentally compatible detergent comprises an alkyl glucoside.

26. The method of embodiment 25, wherein the alkyl glucoside is a decyl glucoside.

27. The method of any one of embodiments 1-24, wherein the environmentally compatible detergent is an alcohol ethoxylate.

28. The method of any one of embodiments 1-24, wherein the environmentally compatible detergent is an alkyl polyethylene glycol ether.

29. The method of any one of embodiments 1-24, wherein the environmentally compatible detergent has a CAS registry number of CAS 9005-64-5, CAS 9005-65-6, CAS 126-43-8, 68515-73-1, CAS 58846-77-8, CAS 59122-55-3, CAS 110615-47-9, CAS 29836-26-8, CAS 64366-70-7, CAS 68937-66-6, CAS 69227-22-1, CAS 25322-68-3. CAS 27252-75-1. CAS 4292-10-8, CAS 132778-08-6, CAS 110615-47-9, CAS 68515-73-1, or CAS 68439-46-3.

30. The method of any one of embodiments 1-29, wherein the detergent comprises one or more surfactants.

31. The method of any one of embodiments 1-30, wherein the detergent comprises one or more surfactants, preservatives, and chelating agents.

32. The method of any one of embodiments 1-31, wherein the feedstream comprises a harvested cell culture fluid.

33. The method of embodiment 32, wherein the detergent is added to the harvested cell culture fluid.

34. The method of any one of embodiments 1-33, wherein the feedstream comprises a capture pool or a recovered product pool.

35. The method of embodiment 34, wherein the capture pool or recovered product pool is an affinity chromatography pool.

36. The method of embodiment 34 or 35, wherein the capture pool or recovered product pool is a protein A pool, a protein G pool or a protein L pool.

37. The method of embodiment 34, wherein the capture pool or recovered product pool is a mixed mode chromatography pool.

38. The method of embodiment 34 or 37, wherein the capture pool is a CaptoAdhere pool.

39. The method of any one of embodiments 1-38, wherein the detergent is used in combination with an anti-foaming agent.

40. The method of embodiment 39, wherein the antifoaming agent is simethicone.

41. The method of any one of embodiments 1-40, wherein the virus is an enveloped virus.

42. The method of any one of embodiments 1-41, wherein the virus is a retrovirus, a herpesvirus, a flavivirus, a poxvirus, a hepadnavirus, a hepatitis virus, an orthomyxovirus, a paramyxovirus, a rhabdovirus, or a togavirus.

43. The method of any one of embodiments 1-42, where in the viral log reduction value (LRV) of the detergent in the feedstream is greater than about one.

44. The method of any one of embodiments 1-43, wherein the viral LRV is greater than about four.

45. The method of embodiment 43 or 44, wherein the LRV is calculated based on infectivity assay.

46. The method of embodiment 45, wherein the infectivity assay is a plaque assay or a TCID50 assay.

47. The method of any one of embodiments 1-46, wherein the method further comprises a step of filtering the feedstream after adding the detergent.

48. The method of embodiment 47, wherein the feedstream is filtered at least about 15 minutes to at least about 48 hours after addition of the detergent.

49. The method of embodiment 47 or 48, wherein the feedstream is filtered at least about 1 hour to at least about 3 hours after addition of the detergent.

50. The method of any one of embodiments 47-49, wherein the feedstream is filtered after about 1 hour after addition of the detergent.

51. The method of any one of embodiments 47-50, wherein the filter is an ultrafilter or a depth filter.

52. The method of any one of embodiments 1-51, wherein the feedstream is subjected to chromatography after addition of the detergent.

53. The method of embodiment 52, wherein the chromatography is one or more of an affinity chromatography, an ion exchange chromatography a hydrophobic interaction chromatography, a hydroxyapatite chromatography, or a mixed mode chromatography.

54. The method of embodiment 53, wherein the affinity chromatography is a protein A chromatography, a protein G chromatography or a protein L chromatography.

55. The method of embodiment 53, wherein the ion exchange chromatography is an anion exchange chromatography or a cation exchange chromatography.

56. The method of embodiment 53, wherein the mixed mode chromatography is a CaptoAdhere chromatography.

57. The method of any one of embodiments 1-56, wherein the therapeutic polypeptide is an antibody, an immunoadhesin, an enzyme, a growth factor, a receptor, hormone, a regulatory factor, a cytokine, an Fc fusion polypeptide, an antigen, or a binding agent.

57. The method of embodiment 56, wherein the antibody is a monoclonal antibody, a chimeric antibody, a humanized antibody, a human antibody, a bispecific antibody, or an antibody fragment.

58. The method of any one of embodiments 1-57, wherein the therapeutic polypeptide is produced in mammalian cells.

59. The method of embodiment 58, wherein the mammalian cell line is a Chinese Hamster Ovary (CHO) cells, or baby hamster kidney (BHK) cells, murine hybridoma cells, or murine myeloma cells.

Each feature disclosed in this specification may be replaced by an alternative feature serving the same, equivalent, or similar purpose. Thus, unless expressly stated otherwise, each feature disclosed is only an example of a generic series of equivalent or similar features.

All references disclosed herein are incorporated herein by reference in their entireties for all purposes.

EXAMPLES

The following Examples are provided to illustrate but not to limit the invention.

Example 1: Evaluation of Detergents

A number of detergents were screened to replace Triton X-100 in processes to purify therapeutic polypeptides and inactivate adventitious agents such as enveloped viruses. Criteria for alternative detergents included but were not limited to any one of non-ionic or zwitterionic nature of detergent, disposability, robust virus inactivation, cost, safety/OSHA, solubility, viscosity, hydrophile/lipophile balance of ~12-15, material availability and source, impact to process and product quality, and stability of raw materials ≥24 months. Examples of detergents evaluated are shown in Table 1.

TABLE 1

Examples of detergents evaluated.

| Used in plasma industry and/or approved GMP raw materials | Alkyl glusocides | "Eco-friendly" | Misc. others |
|---|---|---|---|
| Tri-n-butyl phosphate (TnBP, CAS 126-73-8) | Polyglucoside mixture (CAS 68515-73-1, 58846-77-8, 110615-47-9) | SafeCare 1000 | Tergitol L64 (CAS 9003-11-6) |
| Polysorbate 20 (CAS 9005-64-5) ± TnBP | Triton CG-100 (capry/decyl glucoside, CAS 68515-73-1) | Natsurf 265 (CAS 27252-75-1) | Caprylate acid (CAS 124-07-2) |
| Polysorbate 80 (CAS 9005-64-6) ± TnBP | Mackol DG (lauryl glucoside, CAS 110615-47-9) | Ecosurf EH3 Ecosurf EH6 Ecosurf EH9 (CAS 64366-70-7) | Chembetaine LEC (CAS 4292-10-8) |
| Triton X-100 (CAS 9002-93-1) | APG 325N (CAS 132778-08-6) | Ecosurf SA7 Ecosurf SA9 (CAS 68937-66-6, CAS 69227-22-1, CAS 25322-68-3) | |
| | n-octyl glucoside (CAS 29836-26-8) | Lutensol M5 Lutensol XL (CAS 166736-08-9) Lutensol XP (CAS 160875-66-1) | |
| | n-decyl-beta-D glucopyranoside (CAS 59122-55-3) | Tomadol 900 (CAS 68439-46-3) | |

Several rounds of screening were used to evaluate detergents.

Round 1: Candidate detergents were added to aqueous solutions of monoclonal antibodies (MAbs) to a final concentration of up to 1% (v/v) for three hours at ambient temperature. Three polypeptide solutions were used in these studies. MAb 1 HCCF, was a harvested cell culture fluid obtained in the production of MAb1; Mab3 HCCF, was a harvested cell culture fluid obtained in the production of MAb3; and MAb3 MSS was an adjusted pool fraction following protein A chromatography of a preparation of MAb3. Detergents were evaluated for their effects on mixing, turbidity, product yield, and product quality.

Mixing Studies: Detergents tested were: 1% polysorbate 20±TnBP, 1% polysorbate 80±TnBP, 1% SafeCare 1000, 1% Ecosurf EH-9, 1% Ecosurf EH-6, 1% Ecosurf EH-3, 1% Ecosurf SA9, 1% Ecosurf SA7, 0.1M caprylate, 0.5% or 1% polyglucoside, and 1% Triton X-100. Results were compared to a control where no detergent was added.

Turbidity samples were taken at set time-points 0 hr, 1 hr, 2 hr, 3 hr, after filtration, 1 hr after filtration, and after an overnight hold. Solutions were filtered through a 0.2 μm filter after final mixing time.

Samples were analyzed by purification on PhyTip Protein A followed by size exclusion chromatography (SEC), imaged capillary isoelectric focusing for the charge heterogeneity (icIEF), and capillary electrophoresis for Glycan content. Size exclusion chromatography reveals the presence of low molecular weight species (e.g., degradation products) and high molecular weight species (e.g., aggregates). iCIEF reveals charge variants (e.g., acidic charge variants and basic charge variants). Capillary electrophoresis reveals the glycan structure. Chinese hamster ovary cell proteins (CHOP) levels were tested using an in-house multi-product ELISA. Mab1 or Mab3 concentration was measured in the HCCF using a Protein A HPLC assay and using absorbance at 280 nm for the adjusted protein A pools.

Figure 2:
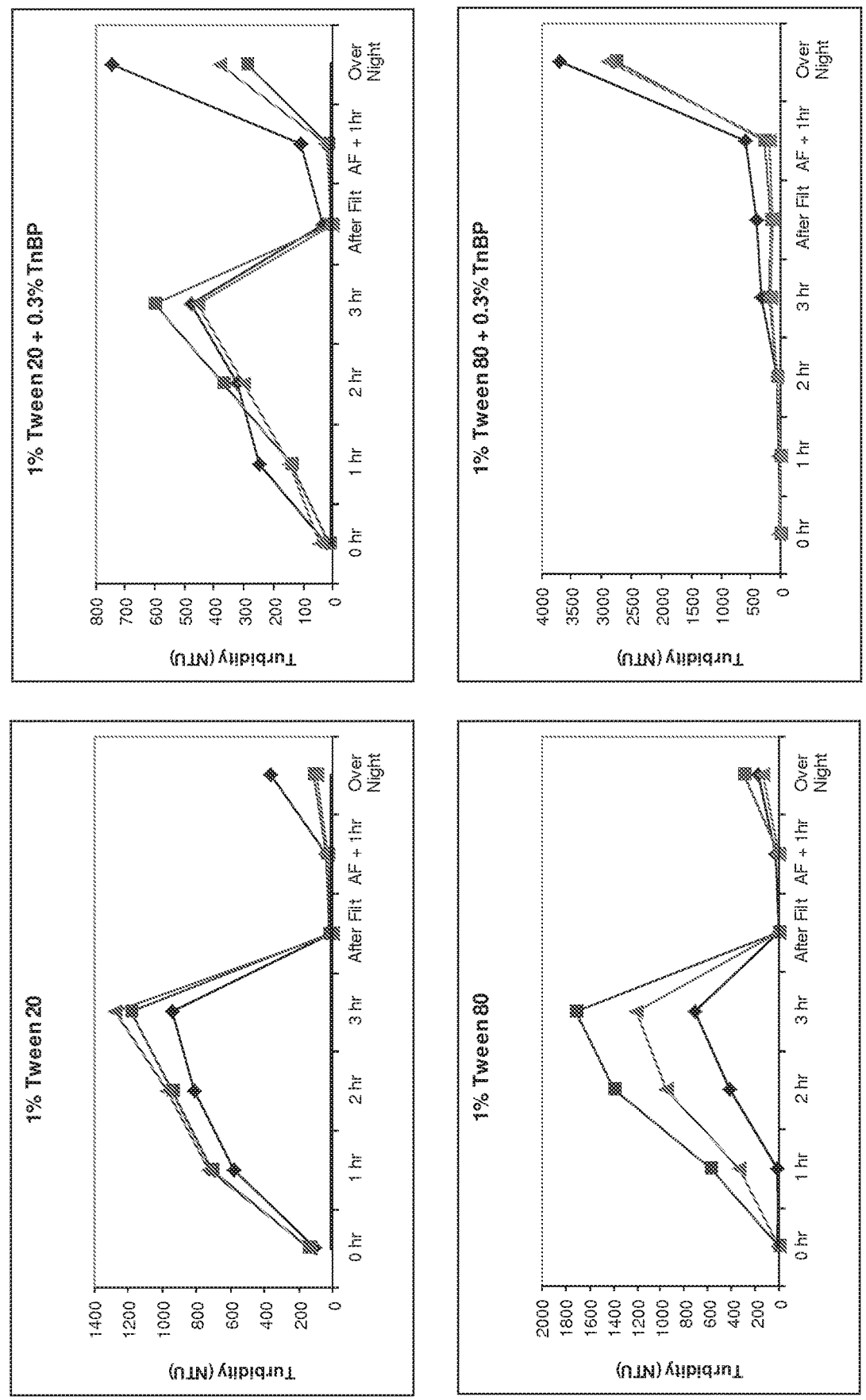
FIG. 2 shows detergent mixing turbidity analysis of MAb1 HCCF treated with 1% Polysorbate 20 (top left), 1% Polysorbate 20 with 0.3% TnBP (top right), 1% Polysorbate 80 (bottom left) and 1% Polysorbate 80 with 0.3% TnBP (bottom right). No mixing (diamonds), stir bar (squares) and overhead agitator (triangles), heavy bar (HCCF control-no mixing).
Figure 3:
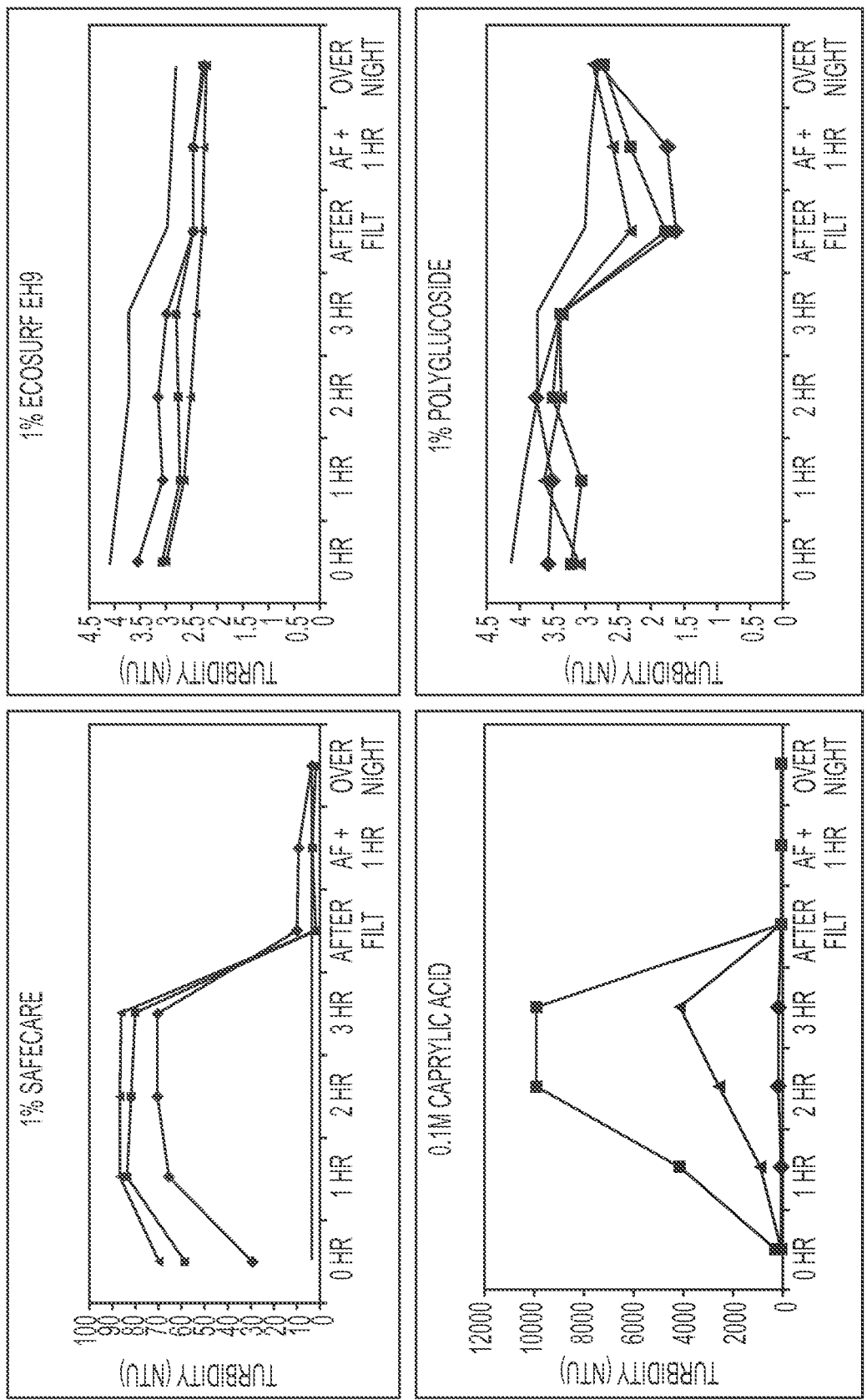
FIG. 3 shows detergent mixing turbidity analysis of MAb1 HCCF treated with 1% SafeCare (top left), 1% Ecosurf EH9 (top right), 0.1 M caprylic acid (bottom left) and 1% decyl polyglucoside (bottom right). No mixing (diamonds), stir bar (squares) and overhead agitator (triangles), heavy bar (HCCF control-no mixing).

FIG. 1 shows detergent mixing turbidity analysis of the MAb1 HCCF control without detergent using various mixing methods. Turbidity of untreated, mixed HCCF had low levels of turbidity that remained unchanged during mixing, filtration, and overnight incubation. Detergent mixing turbidity analysis of MAb1 HCCF treated with 1% polysorbate 20 (top left), 1% polysorbate 20 with 0.3% TnBP (top right), 1% polysorbate 80 (bottom left) and 1% polysorbate 80 with 0.3% TnBP (bottom right) is shown in FIG. 2. Turbidity increased and reformed post-filtration for HCCF treated with polysorbate 20±TNBP or polysorbate 80±TNBP. Detergent mixing turbidity analysis of MAb1 HCCF treated with 1% SafeCare (top left), 1% Ecosurf EH-9 (top right), 0.1 M caprylate (bottom left) and 1% polyglucoside (bottom right) is shown in FIG. 3. Turbidity increased with the addition and mixing of SafeCare or caprylate, however turbidity did not reform after filtration and overnight incubation. No increase in turbidity was observed with the Ecosurf EH-9 or Polyglucoside testing conditions.

Results of detergent mixing on product quality of MAb1 HCCF are shown in Table 2. Increases in high molecular weight species were seen with polysorbate 20 and polysorbate 80 with TnBP. A yield loss and CHOP reduction was seen with caprylate. No changes to glycan or CHOP were seen with other detergents (data not shown).

TABLE 2

Detergent mixing study with MAb1 HCCF product quality.

| Detergent | HCCF turbidity +/− | SEC | | iCIEF | | |
|---|---|---|---|---|---|---|
| | | % HMWS | % LMWS | % Acidic | % Main | % Basic |
| HCCF control | − | 7.5 | 0.1 | 35.1 | 62.6 | 2.3 |
| 1% Ecosurf EH-9 | − | 7.4 | 0.1 | 35.8 | 62.2 | 2.0 |
| 1% SafeCare 1000 | + | 7.4 | 0.1 | 35.2 | 62.5 | 2.3 |

TABLE 2-continued

Detergent mixing study with MAb1 HCCF product quality.

| Detergent | HCCF turbidity +/- | SEC % HMWS | SEC % LMWS | iCIEF % Acidic | iCIEF % Main | iCIEF % Basic |
|---|---|---|---|---|---|---|
| 0.1M caprylate | +++ | NT | NT | NT | NT | NT |
| 1% polyglucoside | − | 7.3 | 0.1 | 36.3 | 61.5 | 2.2 |
| 1% Polysorbate 20 | ++ | 7.3 | 0.1 | 35.0 | 62.5 | 2.5 |
| 1% Polysorbate 20 + TnBP | ++ | 11.8 | 0.1 | 33.1 | 34.9 | 2.0 |
| 1% Polysorbate 80 | ++ | 7.5 | 0.2 | 33.7 | 64.1 | 2.2 |
| 1% Polysorbate 80 + TnBP | ++ | 9.7 | 0.1 | 35.0 | 62.8 | 2.1 |

Results of detergent exposure for three hours on turbidity of MAb3 HCCF and MAb3 MSS pool is shown in Table 3. Significant turbidity was observed for Ecosurf EH-3 and caprylate conditions, minor turbidity for polysorbate 20 or 80 with TnBP and SafeCare.

TABLE 3

Detergent screen with MAb3: HCCF or adjusted protein A pool (MSS)

| Detergent | HCCF turbidity | MSS pool turbidity |
|---|---|---|
| 1% Ecosurf EH-3 | +++ | +++ |
| 1% Ecosurf EH-6 | − | − |
| 1% Ecosurf EH-9 | − | − |
| 1% Ecosurf SA-7 | − | − |
| 1% Ecosurf SA-9 | − | − |
| 1% SafeCare 1000 | + | + |
| 0.5% polyglucoside | − | − |
| 0.1M caprylate | ++ | ++ |
| 1% Triton X-100 | − | − |
| 1% Polysorbate 20 + TnBP | + | + |
| 1% Polysorbate 80 + TnBP | + | + |
| 1% WFI (neg. control) | − | − |

Table 4 shows CHOP and DNA results for detergent screen using MAb3 HCCF and adjusted protein A pools. No impact was observed except CHOP and DNA precipitated in HCCF and ProA pools for caprylate resulting in a 40% product yield loss. No yield loss was noted for the other tested detergents (data not shown).

TABLE 4

Detergent screen using MAb3 HCCF and adjusted protein A pools

| Detergent tested | HCCF + Detergent CHOP (ppm) | HCCF + Detergent DNA (ppm) | Adj. ProA pool + Detergent CHOP (ppm) | Adj. ProA pool + Detergent DNA (ppm) |
|---|---|---|---|---|
| Ecosurf EH3 | 143639 | 365 | 2158 | 3.9 |
| Ecosurf EH6 | 143865 | 448 | 2201 | 4.1 |
| Ecosurf EH9 | 155112 | 418 | 2352 | 4.3 |
| Ecosurf SA7 | 151383 | 483 | 2360 | 5.0 |
| Ecosurf SA9 | 151115 | 465 | 2326 | 4.6 |
| 1% SafeCare 1000 | 153469 | 380 | 2275 | 3.8 |
| 0.5% polyglucoside | 165355 | 328 | 2239 | 3.1 |
| 0.1M caprylate | 12642 | <LOQ | 600 | 0.002 |
| 1% Triton X-100 | 146646 | 261 | 2545 | 2.1 |
| 1% Polysorbate 20 + TnBP | 144016 | 223 | 2229 | 2.6 |
| 1% Polysorbate 80 + TnBP | 130486 | 248 | 2009 | 2.4 |
| 1% WFI (neg. control) | 138286 | 396 | 2298 | 3.6 |

Table 5 shows results of SEC in a detergent screen with MAb3: HCCF or Adj. ProA pool. Treatment with detergent was for three hours at ambient temperature. No significant change in HMW or LMW species were observed except for caprylic acid-treated HCCF resulted in reduction of HMWS to 0.8%.

TABLE 5

Detergent screen witih MAb3: HCCF and Adjusted protein A pool.

| Detergent used | HCCF + Detergent SEC-HMWS (%) | HCCF + Detergent SEC-main (%) | HCCF + Detergent SEC-LMWS (%) | N. ProA pool + detergent SEC-HMWS (%) | N. ProA pool + detergent SEC-main (%) | N. ProA pool + detergent SEC-LMWS (%) |
|---|---|---|---|---|---|---|
| Ecosurf EH3 | 2.1 | 97.8 | 0.1 | 1.8 | 97.8 | 0.1 |
| Ecosurf EH6 | 2.1 | 97.7 | 0.2 | 2.1 | 97.8 | 0.1 |
| Ecosurf EH9 | 2.0 | 97.8 | 0.2 | 2.1 | 97.8 | 0.1 |
| Ecosurf SA7 | 2.2 | 97.6 | 0.1 | 2.1 | 97.8 | 0.1 |
| Ecosurf SA9 | 2.1 | 97.8 | 0.1 | 2.0 | 97.8 | 0.1 |
| 1% SafeCare 1000 | 2.0 | 97.9 | 0.2 | 1.9 | 98.0 | 0.1 |
| 0.5% polyglucoside | 2.1 | 97.8 | 0.2 | 1.9 | 97.9 | 0.1 |
| 0.1M caprylate | 0.8 | 99.1 | 0.1 | 1.8 | 98.1 | 0.1 |
| 1% Triton X-100 | 2.2 | 97.7 | 0.1 | 2.3 | 97.6 | 0.1 |
| 1% Polysorbate 20 + TnBP | 2.1 | 97.7 | 0.2 | 2.1 | 97.8 | 0.1 |
| 1% Polysorbate 80 + TnBP | 2.2 | 97.7 | 0.1 | 2.0 | 97.9 | 0.1 |
| 1% WFI (neg. control) | 2.1 | 97.8 | 0.1 | 1.8 | 98.0 | 0.1 |

Table 6 shows the results of iCIEF in a detergent screen with MAb3 HCCF or Adj. ProA pool. Treatment with detergent was for three hours at ambient temperature. No difference in charge variants was noted except for reduction of acidic peak, increase main peak for Ecosurf SA-9 treated ProA pool. This may be attributed to sample handling and this detergent condition was retested in the subsequent experiment with MAb3 with no changes to the charge profile noted.

TABLE 6

Detergent screen with MAb3: HCCF and adjusted ProA pool.

| Detergent used | HCCF + Detergent iCIEF-acidic (%) | HCCF + Detergent iCIEF-main (%) | HCCF + Detergent iCIEF-basic (%) | N. ProA pool + detergent iCIEF-acidic (%) | N. ProA pool + detergent iCIEF-main (%) | N. ProA pool + detergent iCIEF-basic (%) |
|---|---|---|---|---|---|---|
| Ecosurf EH3 | 59.4 | 37.8 | 2.81 | 50.7 | 46.0 | 3.29 |
| Ecosurf EH6 | 59.3 | 38.0 | 2.64 | 51.8 | 44.9 | 3.27 |
| Ecosurf EH9 | 59.6 | 37.9 | 2.52 | 51.4 | 45.0 | 3.53 |
| Ecosurf SA7 | 59.3 | 38.2 | 2.48 | 51.6 | 45.2 | 3.22 |
| Ecosurf SA9 | 59.8 | 37.8 | 2.43 | 15.7 | 84.3 | 0 |

TABLE 6-continued

Detergent screen with MAb3: HCCF and adjusted ProA pool.

| | HCCF + Detergent | | | N. ProA pool + detergent | | |
|---|---|---|---|---|---|---|
| Detergent used | iCIEF-acidic (%) | iCIEF-main (%) | iCIEF-basic (%) | iCIEF-acidic (%) | iCIEF-main (%) | iCIEF-basic (%) |
| 1% SafeCare 1000 | 59.4 | 38.0 | 2.59 | 52.3 | 44.4 | 3.34 |
| 0.5% polyglucoside | 59.8 | 37.3 | 2.91 | 51.4 | 45.3 | 3.32 |
| 0.1M caprylate | 57.5 | 39.8 | 2.71 | 52.0 | 44.6 | 3.38 |
| 1% Triton X-100 | 59.8 | 37.6 | 2.65 | 51.1 | 45.4 | 3.51 |
| 1% Polysorbate 20 + TnBP | 59.5 | 38.0 | 2.60 | 51.5 | 45.1 | 3.43 |
| 1% Polysorbate 80 + TnBP | 59.6 | 37.5 | 2.86 | 50.7 | 45.6 | 3.69 |
| 1% WFI (neg. control) | 59.8 | 37.4 | 2.85 | 51.7 | 44.8 | 3.58 |

Caprylate and EcoSurf EH-3 were eliminated from further screening due to precipitation and yield loss.

Round 2: Candidate detergents were added to aqueous solutions of monoclonal antibodies (MAbs) to a final concentration of 1% (v/v) overnight at ambient temperature. Detergents were evaluated for their effects on chromatography performance, step yield, and product quality impact on MAb3. Product quality was tested using SEC HPLC to measure size variants (HMW and LMW) and IEC (with carboxypeptidase treatment) to measure charge variants. Glycation was measured using boronate affinity chromatography as described by Zhang et. Al. (Analytical Chem. 2008, 80: 2379-2390). Tryptic peptide mapping was also employed to elucidate other changes to the protein, such as oxidation or deamidation. Process impurity clearance was measured using a multi-product CHOP ELISA, Leached Protein A (LpA) ELISA, and TaqMan PCR assay for DNA quantitation.

Table 7 shows detergent evaluation using MAb3 HCCF with overnight treatment with detergent followed by purification using MabSelect SuRe Protein A chromatography. An atypical chromatogram and low step yield on MabSelect SuRe was observed for the Ecosurf SA7-treated sample. No significant impact to CHOP or DNA clearance was observed. The levels of DNA in the detergent-treated HCCF were variable, which may indicate some interference of the detergent in the sample on the DNA assay. This will be investigated further with the final detergent candidates. The levels of leached Protein A were comparable for each of the tested detergent conditions. No changes to the glycation profiles were noted for any of the detergents tested.

TABLE 7

Detergent evaluation using MAb3 HCCF.

| Detergent | Yield % | CHOP (ppm) HCCF | CHOP (ppm) Pro A Pool | DNA (ppm) HCCF | DNA (ppm) Pro A Pool | LpA (ppm) Pro A Pool | % Glycation* Pro A Pool |
|---|---|---|---|---|---|---|---|
| Polysorbate 80 | 86 | 150380 | 2259 | 1254 | 13 | 15 | 25.5 |
| SafeCare 1000 | 88 | 123859 | 1537 | 398 | 5 | 13 | 25.3 |
| Polyglucoside | 88 | 135515 | 1719 | 605 | 6 | 16 | 25.5 |
| Ecosurf EH6 | 90 | 129500 | 1951 | 77 | 3 | 17 | 23.5 |
| Ecosurf EH9 | 88 | 112562 | 1971 | 737 | 8 | 14 | 24.2 |
| Ecosurf SA7 | 61 | 97186 | 2439 | 682 | 7 | 15 | 23.4 |
| Ecosurf SA9 | 85 | 130769 | 1969 | 638 | 10 | 14 | 24.9 |
| WFI (neg. control) | 84 | 138909 | 2136 | 134 | 6 | 15 | 23.7 |

Figure 4:
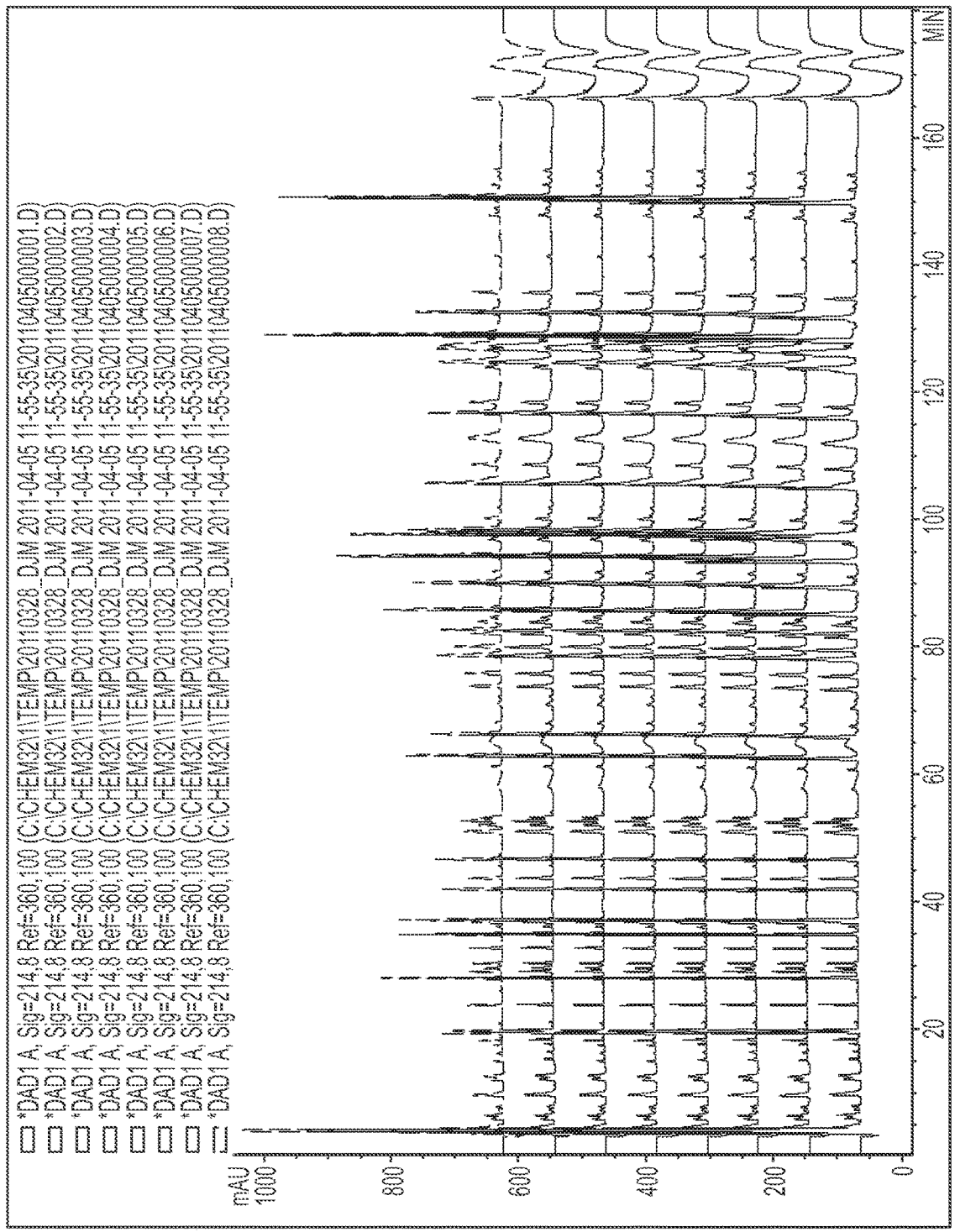
FIG. 4 shows peptide maps of MAb3 following incubation with detergents overnight at ambient temperatures and purification on MAbSelect Sure Protein A.

FIG. 4 shows peptide maps of MAb3 neutralized Protein A pools following incubation with detergents overnight at ambient temperatures and purification on MabSelectSuRe. No difference in product quality was seen for any detergent as evaluated by tryptic peptide mapping.

Table 8 shows results of SEC and IEC analysis of MAb3 HCCF following overnight exposure to candidate detergents. IEC samples were treated with carboxypeptidase B (CpB) prior to analysis. No impact to product quality was seen for any of the tested detergents.

TABLE 8

Detergent evaluation of MAb3 HCCF.

| | Native SEC | | | | | IEC (with CpB) | | |
|---|---|---|---|---|---|---|---|---|
| Detergent | HMWS1 | Dimer | Main Peak | Fab | LMWS1 | Acidic | Main | Basic |
| Polysorbate, 80 | 0.4 | 1.6 | 96.7 | 0.7 | 0.6 | 35.3 | 57.1 | 7.6 |
| SafeCare 1000 | 0.3 | 1.6 | 96.8 | 0.8 | 0.5 | 35.6 | 56.8 | 7.5 |
| Polyglucoside | 0.3 | 1.6 | 96.8 | 0.7 | 0.6 | 35.0 | 57.2 | 7.7 |
| Ecosurf EH6 | 0.3 | 1.6 | 96.8 | 0.7 | 0.6 | 35.2 | 57.2 | 7.7 |
| Ecosurf EH9 | 0.3 | 1.6 | 96.8 | 0.7 | 0.5 | 35.1 | 57.1 | 7.8 |
| Ecosurf SA7 | 0.3 | 1.5 | 97.1 | 0.7 | 0.4 | 36.9 | 55.1 | 8.0 |
| Ecosurf SA9 | 0.3 | 1.6 | 96.8 | 0.8 | 0.5 | 36.8 | 55.4 | 7.8 |
| WFI (neg. control) | 0.4 | 1.6 | 96.7 | 0.8 | 0.6 | 37.0 | 55.3 | 7.7 |

Ecosurf SA-7 was eliminated from further screening due to atypical chromatogram and low yield. Polyglucoside was a mixture of alkyl glucosides and was replaced with individual alkyl glucosides for further studies.

Round 3: Candidate detergents were added to aqueous solutions of monoclonal antibodies (MAbs) to a final concentration of 1% (v/v) overnight at ambient temperature. Polypeptide solutions were used in these studies. MAb 1 HCCF, MAb1 MSS, Mab3, and MAb2 HCCF. Detergents were evaluated for their effects on turbidity, product quality impact and detergent clearance following protein A chromatography.

MAb1, MAb2, and MAb3 HCCF was incubated with 1% (v/v) detergent at ambient temperature overnight. MAb1 was then purified using MabSelect SuRe chromatography. Pooled fractions were analyzed by SEC, iCIEF, and by NMR for detergent clearance testing. Results for turbidity, yield on MabSelect SuRE, and product quality of the adjusted Protein A pools are shown in Table 9. The HCCF treated with 1% polysorbate+0.3% TnBP had high turbidity and low yield on MabSelect SuRe protein A chromatography. This condition also resulted in high amounts of HMW formation. The Lutensol XP90-treated sample had approximately 4% higher levels of acidic variants, compared to the control.

TABLE 9

Detergent evaluation of MAb1 1.3 HCCF

| Detergent | HCCF Turbidity +/− | MSS Yield (%) | SEC % HMWS | SEC % Main | iCIEF % Acidic | iCIEF % Main | iCIEF % Basic |
|---|---|---|---|---|---|---|---|
| HCCF control | − | 93 | 8.3 | 91.7 | 39.46 | 58.99 | 1.55 |
| Ecosurf EH9 | − | 94 | 8.5 | 91.5 | 41.37 | 57.5 | 1.12 |
| Tomadol 900 | − | 97 | 8.2 | 91.8 | 39.11 | 59.43 | 1.47 |
| Triton CG-110 | − | 107 | 7.4 | 92.6 | 38.09 | 60.08 | 1.83 |
| APG 325N | − | 97 | 8.3 | 91.6 | 37.78 | 60.55 | 1.67 |
| Lutensol XP90 | − | 98 | 8.5 | 91.4 | 44.12 | 54.33 | 1.55 |
| Polysorbate 80 + 0.3% TNBP | +++ | 43 | 94.1 | 5.5 | Not tested | Not tested | Not tested |

Detergent clearance during protein A chromatography was evaluated by NMR of neutralized protein A pools and are shown in Table 10. All detergents clear to very low levels during Protein A chromatography.

TABLE 10

Detergent evaluation with MAb1 HCCF, NMR analysis.

| Detergent | NMR Quantitation of detergent in Neutralized Protein A Pool (µg/mL) |
|---|---|
| Ecosurf EH9 | <2 |
| Tomadol 900 | <2 |
| Triton CG-110 | 2.17 |
| APG 325N | <2 |
| Lutensol XP90 | <2 |

Similar analysis was performed with PhyTip Protein A purification followed by SEC-HPLC, iCIEF and CE for glycans using MAb3 HCCF (Table 11) and MAb2 HCCF (Table 12).

TABLE 11

Detergent evaluation with MAb3 HCCF.

| Detergent | HCCF Turbidity +/− | SEC % HMWS | SEC % Main | iCIEF % Acidic | iCIEF % Main | iCIEF % Basic |
|---|---|---|---|---|---|---|
| APG 325N | − | 1.5 | 0.1 | 57.9 | 37.7 | 4.4 |
| Ecosurf EH9 | − | 1.4 | 0.1 | 58.3 | 38.5 | 3.2 |
| Triton CG-110 | − | 1.6 | 0.1 | 59.1 | 37.8 | 3.1 |
| Tomadol 900 | − | 1.4 | 0.1 | 58.2 | 38.7 | 3.1 |
| Lutensol XP90 | − | 1.4 | 0.1 | 58.4 | 38.3 | 3.3 |
| Tergitol L64 | − | 1.4 | 0.1 | 59.5 | 38.3 | 2.2 |
| WFI (neg. control) | − | 1.3 | 0.1 | 59.6 | 36.7 | 3.7 |

No turbidity or significant changes in product quality were seen for MAb3 for any of the tested detergents, relative to the control. No changes in glycan distribution were observed (data not shown).

TABLE 12

Detergent evaluation with MAb2 HCCF.

| Detergent | HCCF Turbidity +/− | SEC % HMWS | SEC % Main | iCIEF % Acidic | iCIEF % Main | iCIEF % Basic |
|---|---|---|---|---|---|---|
| APG 325N | − | 2.0 | 0.1 | 35.7 | 49.3 | 15.0 |
| Ecosurf EH9 | − | 2.0 | 0.1 | 33.8 | 52.1 | 14.1 |
| Triton CG-110 | − | 2.0 | 0.1 | 35.8 | 49.2 | 15.0 |
| Tomadol 900 | − | 1.9 | 0.1 | 34.1 | 51.5 | 14.4 |
| Lutensol XP90 | − | 2.0 | 0.1 | 36.9 | 49.6 | 13.5 |
| Tergitol L64 | − | 2.0 | 0.1 | 36.1 | 49.7 | 14.2 |
| WFI (neg. control) | − | 2.0 | 0.1 | 33.3 | 53.4 | 13.3 |

No turbidity or significant changes in product quality were seen for MAb2 for any of the tested detergents, relative to the control. Slightly higher percent acidic species were seen with Lutensol XP90 and Tergitol L64. No changes in glycan distribution were observed (data not shown).

From this round of testing, Polysorbate 80+TnBP was eliminated due to turbidity and product quality impact for MAb1.

Detergents were also evaluated for virus inactivation (xMuLV) in MAb1 HCCF at 20° C. Detergent was added to MAb1 HCCF to a final concentration of 0.3%. The detergent containing material was spiked with 5% v/v with XMuLV. Samples were incubated for 30 minutes to 6 hours at 20° C. and assayed for the presence of Xenotropic Murine Leukemia Virus (XMuLV), a model retrovirus. The presence of XMuLV was determined by a TCID50 assay utilizing PG-4 indicator cells. Virus inactivation results are presented as LRV (Log Reduction Value) and are shown in Table 13.

TABLE 13 xMuLV Inactivation with MAb1 HCCF$^a$ at 20° C.

| Detergent | Time 0.5 | 1 | 2 | 3 | 6 |
|---|---|---|---|---|---|
| 1% Polysorbate 80 | NT | 3.3 | NT | 5.7 | NT |
| 1% Polysorbate 80 (Protein A pool) | 0.4 | 0.9 | 1.2 | 1.1 | NT |
| 2% Polysorbate 80 (Protein A pool) | 0.7 | 0.7 | 1.2 | 1.0 | NT |
| 1% Polysorbate 80 + 0.3% TNBP | NT | 5.2 | NT | ≥5.5 | NT |
| 1% Polysorbate 20 | 1.0 | 1.4 | NT | 2.3 | 4.5 |
| 2% Polysorbate 20 | 0.6 | 0.7 | NT | 2.2 | 5.6 |

TABLE 13-continued xMuLV Inactivation with MAb1 HCCF$^a$ at 20° C.

| Detergent | Time | | | | |
|---|---|---|---|---|---|
| | 0.5 | 1 | 2 | 3 | 6 |
| 1% Polysorbate 20 + 0.3% TNBP | NT | ≥5.7 | NT | NT | NT |
| 1% TnBP | NT | 2.9 | NT | NT | NT |
| 1% polyglucoside | NT | ≥5.1 | NT | ≥5.1 | NT |
| 0.1M caprylate pH 7.6 | NT | NT | ≥6.0 | ≥6.0 | NT |
| 0.1M caprylate pH 5.0 | NT | NT | ≥5.1 | ≥5.1 | NT |
| 0.03M caprylate pH 7.6 | NT | NT | 0.21 | 0.30 | NT |
| 0.03M caprylate pH 4.5 | NT | NT | ≥5.0 | ≥5.0 | NT |
| SafeCare 1000 0.5% | NT | NT | ≥5.1 | 5.7 | NT |
| SafeCare 1000 1.0% | NT | NT | ≥5.5 | ≥5.5 | NT |
| SafeCare 1000 2.0% | NT | NT | ≥5.2 | ≥5.2 | NT |
| SafeCare 1000 1.0% SC/solvent 70/30 | NT | NT | ≥5.2 | ≥5.2 | NT |
| 1% Ecosurf EH-6 | NT | NT | ≥4.7 | ≥4.7 | NT |
| 1% Ecosurf EH-9 | NT | NT | ≥5.1 | ≥5.1 | NT |

$^a$Feedstock used is HCCF unless otherwise specified.

xMuLV inactivation was less effective with Polysorbate 80, Polysorbate 20 or TnBP alone. Precipitation was noted with caprylate samples.

Polysorbate 80 with and without solvent was evaluated for virus inactivation (XMuLV) in a more downstream pool using rProtein1 CaptoAdhere pool at room temperature. XMuLV inactivation results are presented in Table 14. Effective XMuLV inactivation was obtained in 1 hour with Polysorbate 80 alone. Complete virus inactivation was observed within 5 minutes with Polysorbate 80 with solvent.

TABLE 14

XMuLV inactivation with Polysorbate 80 with and without solvent in rProtein1 CaptoAdhere Pool at Room Temperature.

| Time (min) | 1% Polysorbate 80 | | 1% Polysorbate 80 + 0.3% TNBP | |
|---|---|---|---|---|
| | LRV | | | |
| | Run 1 | Run 2 | Run 1 | Run 2 |
| 5 | .45 | NT | ≥3.1 | ≥4.8 |
| 10 | .57 | NT | ≥3.1 | ≥4.8 |
| 15 | .82 | NT | ≥3.1 | NT |
| 30 | 2.1 | NT | ≥3.1 | NT |
| 60 | ≥3.4 | ≥4.5 | ≥3.1 | NT |
| 90 | ≥3.4 | ≥4.5 | ≥3.1 | NT |
| 120 | ≥3.4 | ≥5.0 | ≥3.1 | NT |

NT = not tested

XMuLV inactivation in MAb2 HCCF by candidate detergents is presented in Table 15. Complete and effective virus inactivation was achieved at 1 hour at 20° C. for all tested detergents at 0.5% and 1% concentrations.

TABLE 15

Virus inactivation of MAb3 at 20° C. 20° C., 1 hour

| Detergent | 1% Detergent | 0.5% Detergent |
|---|---|---|
| Triton CG-110 | ≥5.6 | ≥5.7 |
| APG 325N | ≥5.4 | ≥5.5 |
| Lutensol XP90 | ≥5.1 | ≥5.2 |
| Tomadol 900 | ≥4.8 | ≥4.9 |
| Ecosurf EH-6 | ≥4.8 | NT |
| Ecosurf EH-9 | NT | ≥4.9 |

NT = not tested

XMuLV inactivation in MAb2 HCCF and rProtein1 HCCF by candidate detergents at concentrations of 0.3% and 0.5% and lower temperature of 12° C. is presented in Table 16. Effective virus inactivation was achieved at 1 hour at 12° C. for all tested detergents at 0.3% and 0.5% concentrations, except for Tergitol L64 which was not effective. Tergitol L64 was thus removed from further consideration.

TABLE 16

XMuLV inactivation of Mab2 and rProtein 1 at lower temperature and detergent concentration

| Detergent | MAb 2 | | rProtein1 | |
|---|---|---|---|---|
| | 1 hr | 3 hrs | 1 hr | 3 hrs |
| 12° C., 0.5% Detergent | | | | |
| Triton CG-110 | ≥5.4 | ≥5.4 | ≥5.9 | ≥5.9 |
| APG 325N | ≥5.2 | ≥5.2 | ≥5.7 | ≥5.7 |
| Lutensol XP90 | ≥4.9 | 5.2 | ≥5.4 | ≥5.4 |
| Tomadol 900 | ≥4.6 | ≥4.6 | ≥5.1 | ≥5.1 |
| Ecosurf EH-9 | ≥4.6 | ≥4.6 | ≥5.1 | ≥5.1 |
| Tergitol L64 | NT | NT | 0.0 | 0.2 |
| 12° C., 0.3% Detergent | | | | |
| Triton CG-110 | 6.0 | NT | ≥5.5 | ≥5.5 |
| APG 325N | 5.5 | NT | 5.9 | 5.9 |
| Lutensol XP90 | ≥6.0 | NT | ≥5.6 | ≥5.6 |
| Tomadol 900 | NT | NT | NT | NT |
| Ecosurf EH-9 | 5.8 | NT | 5.0 | NT |
| Tergitol L64 | NT | NT | NT | NT |

NT = not tested

XMuLV inactivation in rProtein2 HCCF with varying concentrations of Triton CG-110 is presented in Table 17. Concentration dependent virus inactivation was observed. At 0.05% Triton CG-110 concentration inactivation is ineffective wherein less than 1 LRV was obtained.

TABLE 17

XMuLV inactivation rProtein 2 HCCF at 12° C., 1 hour

| Triton CG-110 Concentration (%) | LRV |
|---|---|
| 0.05 | 0.1 |
| 0.10 | 1.1 |
| 0.15 | 2.3 |
| 0.20 | 3.6 |
| 0.25 | 5.8 |
| 0.30 | ≥5.4 |
| 0.35 | ≥5.4 |
| 0.40 | 5.8 |

Example 2: Use of Simethicone for Foaming Mitigation: Impact of Virus Inactivation The use of simethicone to mitigate foaming issues for Triton CG110 was evaluated for impact on virus inactivation.

Detergent (0.3%) was added to rProtein3 HCCF with or without simethicone, an anti-foaming agent, at a final concentration of 0.1%. Samples were evaluated for virus inactivation (xMuLV). Results are shown in Table 18. There was no impact by 0.1% simethicone on the inactivation of xMuLV by Triton CG110.

TABLE 18

Use of simethicone for foaming mitigation has not impact of viral inactivation by Triton CG110.

| Timepoint | Detergent, No simethicone | Detergent + 0.1% simethicone |
|---|---|---|
| T = 0 (starting virus titer) | 7.4 TCID$_{50}$ | 7.31 TCID$_{50}$ |
| T = 30 min | 5.84 LRV | ≥5.43 LRV |
| T = 60 min | 5.84 LRV | ≥5.43 LRV |

The ability of detergents to inactivate other enveloped viruses was also evaluated. Detergent was added to rProtein 1 HCCF to a final concentration of 0.3%. The detergent containing material was spiked with 5% v/v with each virus separately. Samples were incubated for 1 and/or 3 hours at 12° C. and assayed for the presence of XMuLV, pseudorabies virus (PRV) or bovine viral diarrhea virus (BVDV). The presence of the viruses was determined using cell based infectivity assays. XMuLV was determined by a TCID$_{50}$ assay utilizing PG-4 indicator cells. The presence of PRV and BVDV was determined by a plaque assay utilizing CV-1 and BT indicator cells, respectively. Results are presented in Table 19. APG325N and Triton CG 110 provided effective inactivation for all three viruses.

TABLE 19

Viral inactivation of enveloped viruses in rProtein1, 12° C., 1 hour

| Virus | Family | Size (nm) | Resistance to physic-chemical treatment | Time | Ecosurf EH-9 | APG 325N | Lutensol XP90 | Triton CG 110 |
|---|---|---|---|---|---|---|---|---|
| X-MuLV | Retroviridae | 80-110 | Low | 1 hr | 5.0 | 5.9 | >5.6 | >5.5 |
|  |  |  |  | 3 hrs | NT | 5.9 | >5.6 | >5.5 |
| PRV | Herpesviridae | 150-200 | Med | 1 hr | 0.2 | >5.1 | 0.1 | 6.1 |
| BVDV | Flaviviridae | 50-70 | Low | 1 hr | 5.8 | >6.5 | >6.4 | >6.5 |

The ability of Triton CG 110 and Ecosurf EH-9 to inactivate enveloped virus were compared to that of Triton X-100. Triton CG 110, Triton X-100 or Ecosurf EH-9 was added to rProtein2 HCCF at a final concentration of 0.3%. The detergent containing material was spiked with 5% v/v with PRV and BVDV separately. Samples were incubated for 30 minutes and 1 hour at 20° C. and assayed for the presence of pseudorabies virus (PRV) or bovine viral diarrhea virus (BVDV) using plaque assay. Log reduction values of virus were determined. Results are shown in Table 20.

TABLE 20

Viral inactivation with Triton X-100, Triton CG 110 and Ecosurf EH-9, 20° C., 0.3% Detergent in rProtein 2 HCCF

| Virus | Time (min) | Triton X-100 Run 1 | Triton X-100 Run 2 | Triton CG 110 Run 1 | Triton CG 110 Run 2 | Ecosurf EH-9 Run 1 | Ecosurf EH-9 Run 2 |
|---|---|---|---|---|---|---|---|
| PRV | 30 | >5.8 | >5.3 | 5.7 | >6.3 | >5.7 | >5.2 |
|  | 60 | >5.8 | >5.3 | 5.9 | 5.9 | >5.7 | >5.2 |
| BVDV | 30 | 5.4 | 5.5 | >6.4 | 5.9 | >6.0 | 6.0 |
|  | 60 | >5.4 | >5.5 | >6.4 | >6.5 | 5.7 | 5.7 |

Ecosurf EH-9 and Triton CG 110 provided effective inactivation that is comparable to Triton X-100.

Example 3: Screen with Additional Molecules

Detergents with or without simethicone were further screened for product quality. The following conditions were tested.
1. Control HCCF (no detergent)
2. HCCF+0.1% simethicone
3. HCCF+Ecosurf EH9
4. HCCF+0.7% Triton CG110
5. HCCF+0.7% Triton CG110+0.1% simethicone.

Samples were incubated at ambient temperature for 15 hours, and then stored at 2-8° C. Samples were analyzed from product quality following Phytip protein A purification and by SEC, iCIEF, and glycan analysis. HCCF included HCCF MAb4, MAb5, MAb6, MAb7, MAb3, MAb8, and MAb9. Results are shown in Tables 21-26.

Results for detergent±simethicone treatment of Mab4 HCCF are shown in Table 21. No impact to product quality was noted for each of the tested conditions. No changes to glycans were observed (data not shown).

TABLE 21

Screening additional molecules: impact on product quality of MAb4

| Detergent | Simeth-icone | SEC HMW (%) | SEC Main (%) | SEC LMW (%) | iCIEF Acidic (%) | iCIEF Main (%) | iCIEF Basic (%) |
|---|---|---|---|---|---|---|---|
| Control | — | 1.09 | 98.7 | 0.26 | 40.78 | 55.45 | 3.77 |
| Control | 0.1% | 1.13 | 98.6 | 0.27 | 40.89 | 55.74 | 3.37 |
| Ecosurf EH-9 | — | 1.11 | 98.6 | 0.26 | 41.06 | 56.47 | 2.47 |
| Triton CG-110 | — | 1.10 | 98.6 | 0.28 | 39.56 | 57.89 | 2.55 |
| Triton CG-110 | 0.1% | 1.15 | 98.6 | 0.28 | 36.84 | 60.86 | 2.3 |

Results for detergent±simethicone treatment of Mab5 HCCF are shown in Table 22. No impact to product quality was noted for each of the tested conditions. No changes to glycans were observed (data not shown).

TABLE 22

Screening additional molecules: impact on product quality of Mab5

| Detergent | Simethicone | SEC HMW (%) | SEC Main (%) | SEC LMW (%) | iCIEF Acidic (%) | iCIEF Main (%) | iCIEF Basic (%) |
|---|---|---|---|---|---|---|---|
| Control | — | 3.59 | 96.4 | 0.04 | 37.48 | 59.66 | 2.86 |
| Control | 0.1% | 3.61 | 96.3 | 0.04 | 36.28 | 60.49 | 3.23 |
| Ecosurf EH-9 | — | 3.56 | 96.4 | 0.05 | 35.42 | 61.75 | 2.83 |
| Triton CG-110 | — | 3.35 | 96.6 | 0.04 | 36.17 | 61.31 | 2.52 |
| Triton CG-110 | 0.1% | 3.37 | 96.6 | 0.04 | 36.54 | 60.4 | 3.07 |

Results for detergent±simethicone treatment of Mab6 HCCF are shown in Table 23. No impact to product quality was noted for each of the tested conditions. No changes to glycans were observed (data not shown).

TABLE 23

Screening additional molecules: impact on product quality of Mab6

| Detergent | Simethicone | SEC HMW (%) | SEC Main (%) | SEC LMW (%) | iCIEF Acidic (%) | iCIEF Main (%) | iCIEF Basic (%) |
|---|---|---|---|---|---|---|---|
| Control | — | 1.62 | 97.8 | 0.58 | 32.85 | 65.08 | 2.07 |
| Control | 0.1% | 1.70 | 97.7 | 0.57 | 34.07 | 63.89 | 2.04 |
| Ecosurf EH-9 | — | 1.58 | 97.8 | 0.60 | 34.55 | 63.36 | 2.09 |
| Triton CG-110 | — | 1.59 | 97.8 | 0.57 | 35.19 | 62.67 | 2.15 |
| Triton CG-110 | 0.1% | 1.78 | 97.6 | 0.58 | 33.31 | 64.41 | 2.29 |

Results for detergent±simethicone treatment of Mab7 HCCF are shown in Table 24. No significant impact to product quality was noted for each of the tested conditions. Slightly higher % acidic and lower % basic variants were observed in the Triton CG-110-treated samples. No changes to glycans were observed (data not shown).

TABLE 24

Screening additional molecules: impact on product quality of Mab7

| Detergent | Simethicone | SEC HMW (%) | SEC Main (%) | SEC LMW (%) | iCIEF Acidic (%) | iCIEF Main (%) | iCIEF Basic (%) |
|---|---|---|---|---|---|---|---|
| Control | — | 3.75 | 96.2 | 0.03 | 30.62 | 66.1 | 3.28 |
| Control | 0.1% | 3.82 | 96.2 | 0.02 | 31.67 | 65.17 | 3.16 |
| Ecosurf EH-9 | — | 3.82 | 96.2 | 0.02 | 31.71 | 64.02 | 4.27 |
| Triton CG-110 | — | 3.78 | 96.2 | 0.02 | 35.39 | 63.18 | 1.43 |
| Triton CG-110 | 0.1% | 3.77 | 96.2 | 0.02 | 32.48 | 65.69 | 1.83 |

Results for detergent simethicone treatment of Mab8 HCCF are shown in Table 25. No impact to product quality was noted for each of the tested conditions. No changes to glycans were observed (data not shown).

TABLE 25

Screening additional molecules: impact on product quality of Mab8

| Detergent | Simethicone | SEC HMW (%) | SEC Main (%) | SEC LMW (%) | iCIEF Acidic (%) | iCIEF Main (%) | iCIEF Basic (%) |
|---|---|---|---|---|---|---|---|
| Control | — | 2.07 | 97.8 | 0.15 | 28.96 | 60.5 | 10.54 |
| Control | 0.1% | 2.10 | 97.7 | 0.15 | 28.2 | 61.26 | 10.54 |
| Ecosurf EH-9 | — | 2.06 | 97.8 | 0.16 | 28.04 | 61.51 | 10.45 |
| Triton CG-110 | — | 2.04 | 97.8 | 0.16 | 28.67 | 60.96 | 10.37 |
| Triton CG-110 | 0.1% | 2.05 | 97.8 | 0.15 | 28.31 | 61.28 | 10.41 |

Results for detergent simethicone treatment of Mab9 HCCF are shown in Table 26. No impact to product quality was noted for each of the tested conditions. No changes to glycans were observed (data not shown).

TABLE 26

Screening additional molecules: impact on product quality of Mab9

| Detergent | Simethicone | SEC HMW (%) | SEC Main (%) | SEC LMW (%) | ICIEF Acidic (%) | iCIEF Main (%) | ICIEF Basic (%) |
|---|---|---|---|---|---|---|---|
| Control | — | 6.76 | 93.0 | 0.25 | 44.65 | 41.07 | 14.29 |
| Control | 0.1% | 6.95 | 92.9 | 0.14 | 42.2 | 43.11 | 14.69 |
| Ecosurf EH-9 | — | 6.74 | 93.1 | 0.11 | 43.98 | 42.37 | 13.65 |
| Triton CG-110 | — | 6.71 | 93.2 | 0.12 | 42.21 | 41.98 | 15.81 |
| Triton CG-110 | 0.1% | 6.76 | 93.1 | 0.12 | 44.64 | 42.76 | 12.6 |

Example 4: Sparging Studies

Four detergents under consideration were evaluated for foaming and the effectiveness of simethicone for foaming mitigation.

The detergents evaluated included APG 325, Triton CG 110, Ecosurf EH9 and Lutensol XP 90. Detergent (0.5%) was added to HCCF in a two liter fermenter. Solutions were mixed at a rate of 50 RPM. Fermenters were either sparged or not sparged with house air at a rate of 10 standard cubic centimeters per minute (SSCM). An antifoam agent, 1% simethicone, was added at 2 mL/L culture.

Ecosurf EH9 showed less foaming and had smaller bubbles than the alkyl glucoside detergents. The addition of antifoam agent removed all foam and additional foam did not re-form over 72 hours.

Triton CG 110 showed large, airy bubbles. Addition of antifoam reduced but did not totally remove foam. Additional foam did not form over 72 hours.

APG 325N showed the rapid formation of large airy bubbles that foamed out of the vessel. Addition of antifoam had minimal effect of foam and additional foam formed after the addition of antifoam. In contrast, addition of APG 325N to HCCF that was not sparged had little or no foam.

Example 5: Stability of Two Detergents

Instability of Ecosurf EH9 was noted by NMR analysis. A 10% stock solution of Ecosurf EH9 was held at room temperature and at 40 C and analyzed by NMR at days 0, 7, 15, and 36. Results are shown in Table 17. Degradation and the formation of aromatics was detected.

Figure 5:
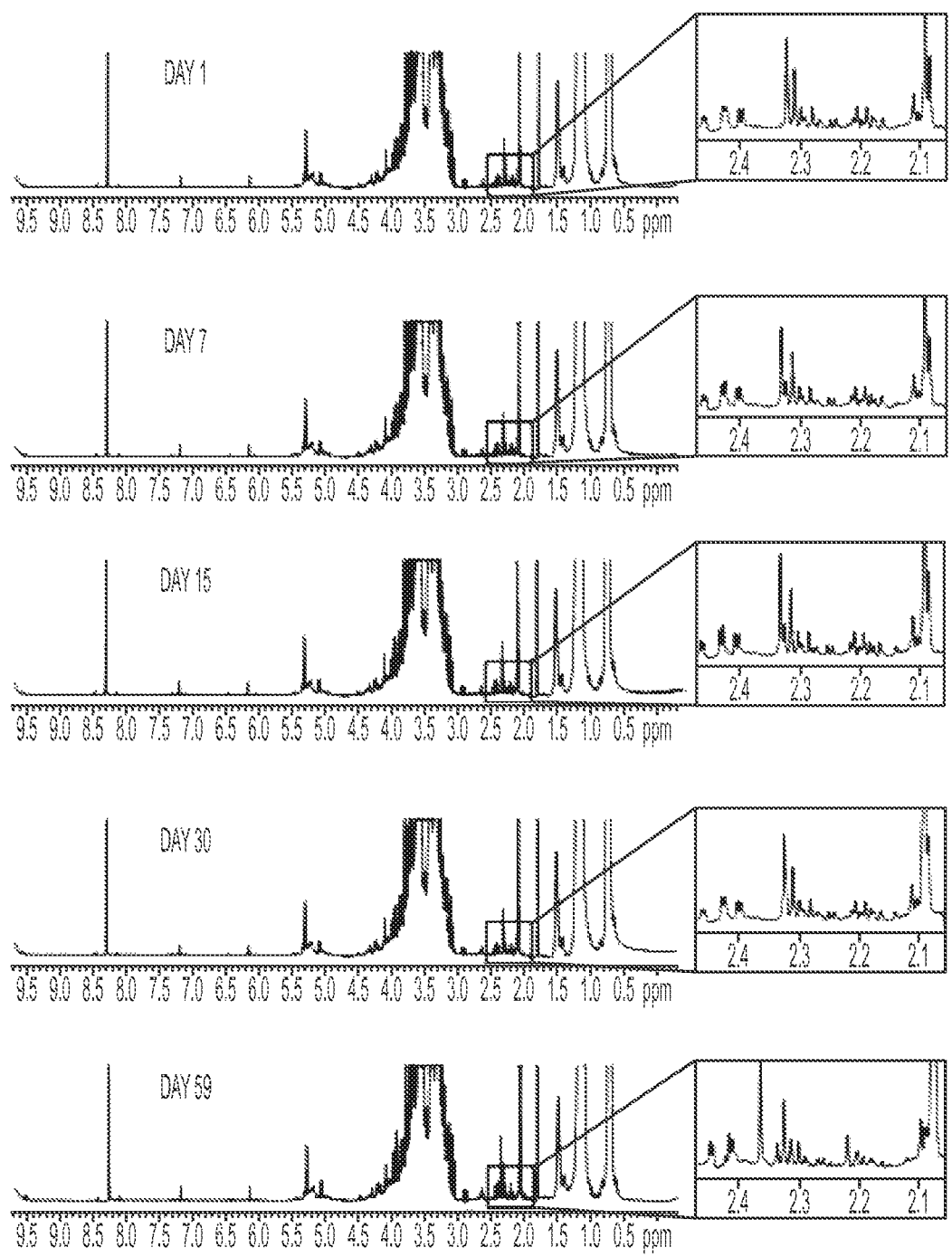
FIG. 5 shows the NMR spectra of 10% Triton CG-110 stability samples held for various timepoints up to 59 days at 40° C.
Figure 6:
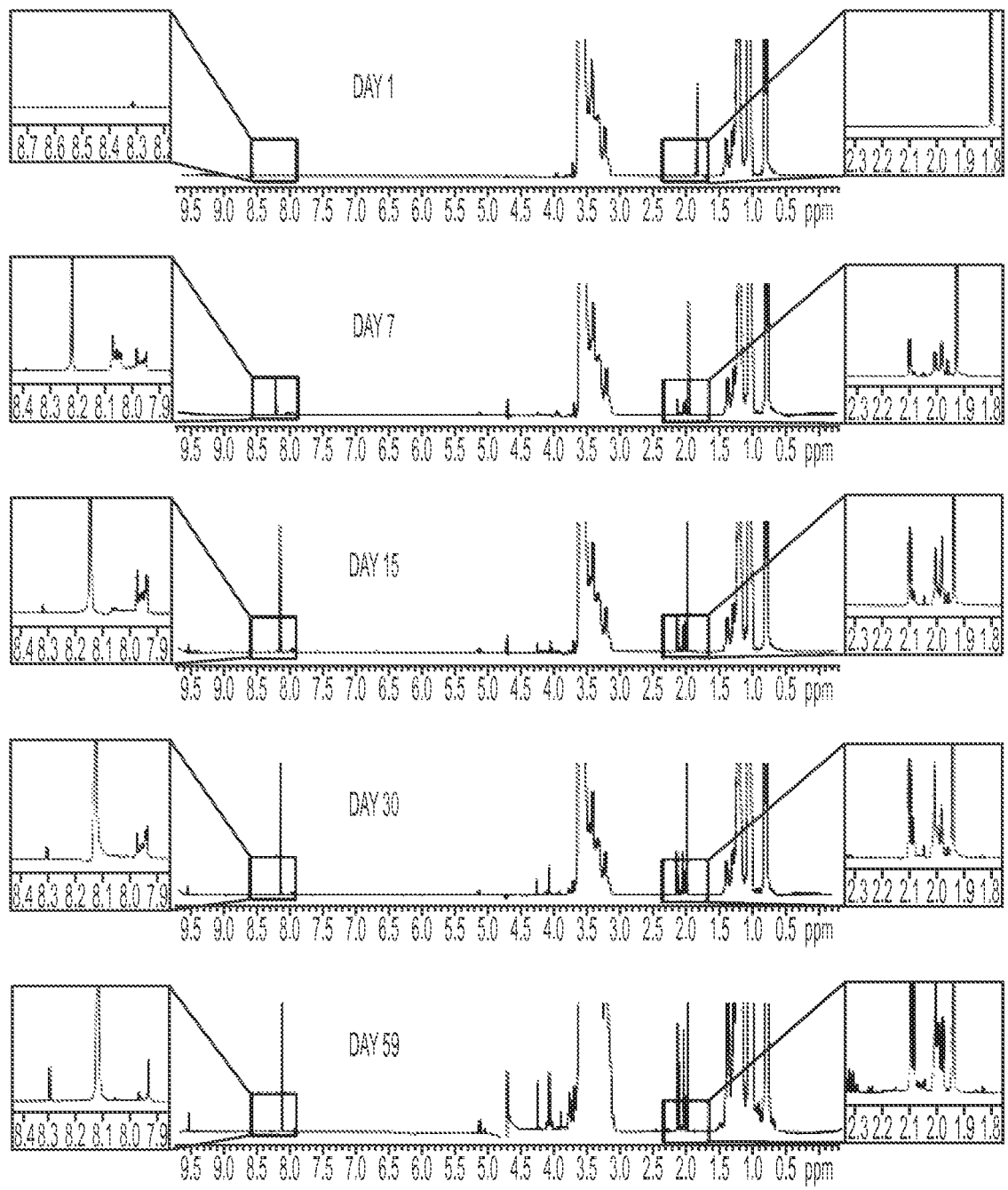
FIG. 6 shows the NMR spectra of 10% Ecosurf EH-9 stock solution stability samples held for various timepoints up to 59 days at 40° C.

Instability of Ecosurf EH-9 was noted by NMR analysis. 10% stock solutions of Ecosurf EH-9 and Triton CG-110 were held at room temperature and at 40 C and analyzed by NMR at days 0, 7, 15, and 30, and 59. Results for quantitation of Ecosurf EH-9 degradation products are shown in Table 27. Degradation and the formation of aromatics was detected for Ecosurf EH-9. FIGS. 5 and 6 show the NMR spectra for stability samples of Triton CG-110 and Ecosurf EH-9, respectively. Triton CG-110 is stable, with little changes up to 59 days. In contrast, formation of the degradation products during storage of the Ecosurf EH-9 solution can be visualized.

TABLE 27

Instability of Ecosurf EH9.

| Sample | Total Degraded (μg/mL) | Total Aromatics (μg/mL) |
|---|---|---|
| Day 0 40° C. | 98.9 | 1.0 |
| Day 7 40° C. | 234.5 | 50.5 |
| Day 15 40° C. | 392.9 | 106.5 |
| Day 36 40° C. | 630.1 | 174.9 |
| Day 36 Room Temp | 115.1 | 8.8 |

In addition, Ecosurf EH9 and Triton CG 110 were analyzed for the formation of peroxide in a 10% (v/v) aqueous stock of detergent over a course of eight weeks. The EMD Millipore colorimetric peroxide test 1.10001.0001 test was used. Results in ppm are shown in Table 28. Raw materials and stock solutions were stored at ambient temperature and protected from light with foil overlay. Ecosurf EH9 raw material had been opened and resealed approximately eight months earlier. Peroxide was detected in Ecosurf EH9 raw material and 10% stock solutions. No detectable peroxide (<0.5 ppm) was detected in stock solutions of Triton CG110 over eight weeks.

TABLE 28

Formation of peroxide (ppm levels).

| Detergent | Lot # | Comment | T = 0 Apr. 18, 2013 | T = 2 weeks | T = 4 weeks | T = 6 weeks | T = 8 weeks |
|---|---|---|---|---|---|---|---|
| Ecosurf EH9 | A | Clear phase | <0.5 | | ~2 | | |
| Ecosurf EH9 | A | Precipitate phase | <0.5 | | ~2-3 | | |
| Ecosurf EH9 | A | Mixed | <0.5 | | ~2 | | |
| Ecosurf EH9 | B | Opened RM* | ~0.5 | ~2 | ~4-5 | ~5 | ~7-8 |
| Ecosurf EH9 | B | Sealed RM | <0.5 | | ~4-5 | | |
| Ecosurf EH9 | C | | <0.5 | | ~0.5 | | |
| Ecosurf EH9 | D | | <0.5 | | ~4-5 | | |
| Triton CG 110 | A | Opened RM* | <0.5 | <0.5 | | <0.5 | <0.5 |
| Triton CG 110 | B | | <0.5 | | | <0.5 | <0.5 |

Example 6: EHS Evaluation of Detergents

Twenty one different candidate materials for reviewed for environmental health and safety. Each material was researched to determine its basic physical and toxicological characteristics. This EHS information was obtained from manufacturer and government literature and compiled into Table 29.

TABLE 29

Detergents analyzed

| Material | General characteristics | Biodegradability | Ecotoxity Data (Aquatic Tox) |
|---|---|---|---|
| Tween 20 (Polyoxyethylene (20) monolaurate) CAS #9005-64-5) | Clear yellow liquid, non-ionic surfactant, soluble in water[1] Chemical formulation: $C_{58}H_{114}O_{26}C_{18}H_{34}O_6 \cdot (C_2H_4O)_n$ MW: 1227.54 g/mol | Not available. Poor biodegradability according to Roche's inherent biodegradability test (OECD 302): 40% TOC removal by day 28; anaerobically degradable | Avoid release into the environment Extended ecotoxicity data not available; Chronic toxicity of nonionic surfactants generally occurs at concentrations >0.1 mg/L. Tween 20 may be more toxic than Tween 80 freshwater data: EC50 ≤100 mg/l 3 weeks *Selenastrum capricornutum* acute NOEC 10 mg/l (highest tested concentration, limit test) 48 h *Daphnia magna* OECD202 LC50 350 mg/l 1 d *Poecilia reticulata* chronic NOEC 10 mg/l (highest tested concentration, limit test) 21 d *Daphnia magna* OECD repro preliminary acute-based freshwater PNEC 0.1 mg/l, note this is not solid due to the algal and fish data; no chronic-based PNEC derivable as no chronic algal NOEC (or a chronic fish |

TABLE 29-continued

Detergents analyzed

| Material | General characteristics | Biodegradability | Ecotoxicity Data (Aquatic Tox) |
|---|---|---|---|
| | | | NOEC) is given marine data: acute LC50 1447 mg/l 1 d *Artemia* sp. (marine), chronic NOEC 10 mg/l various (12 species) marine microalgae (both green algae and cyanobactera) 10-12 d chronic NOEC 20 mg/l ~2 d, *Sphaerechinus granularis* (sea urchin embryo-larval test, usually regarded as chronic preliminary chronic-based marine PNEC 0.2 mg/l, a third group of organisms would be necessary for a solid marine PNEC |
| Tween 80 (Polyoxyethylene (20) monolaurate) (CAS #9005-65-6) | Clear yellow to amber liquid, non-ionic surfactants, soluble in water.1 Chemical formulation: C64H124O26 MW: 1309.68 g/mol | Not available. Poor biodegradability according to Roche's inherent biodegradability test (OECD 302): 50% TOC removal by day 28; anaerobically degradable | Extended ecotoxicity data not available Chronic toxicity of nonionic surfactants generally occurs at concentrations >0.1 mg/L. Tween 20 may be more toxic than Tween 80 freshwater: algal NOEC 2 mg/l *Chlorella vulgaris* 96 h; algal $EC_{10}$ (~NOEC) 6.99 mg/l *Scenedesmus quadricauda* 96 h; EC50 ≥100 mg/l, ?NOEC 100 mg/l? 3 weeks *Selenastrum capricornutum* chronic NOEC 100 mg/l 4 d Gloeocapsa (Cyanobacteria) chronic NOEC 250 mg/l 96 h *Tetrahymena pyriformis* mortality NOEC but reproductive parameter (L)OEC 10'000 mg/l single tested concentration 16 d *Oryzias latipes* no acute-based PNEC as no crustacean (daphnid) is available; no chronic-based freshwater PNEC because *Tetrahymena* is not normally used for PNEC derivation and 16-d fish is not really chronic and is a LOEC marine: chronic NOEC 10 mg/l various (12 species) marine microalgae 10-12 d chronic NOEC 20 mg/l ~2 d, *Sphaerechinus granularis* (sea urchin embryo-larval test, usually regarded as chronic preliminary chronic-based marine PNEC 0.2 mg/l, a third or fourth group of organisms would be necessary for a solid marine PNEC |

TABLE 29-continued

Detergents analyzed

| Material | General characteristics | Biodegradability | Ecotoxity Data (Aquatic Tox) |
|---|---|---|---|
| Tributylphosphate (TBP) CAS # 126-73-8) | yellow liquid Slightly soluble in water An organo-phosphorous compound Chemical Formulation: $(C_4H_9O)_3PO$ MW: 266.32 g/mol | water, TBP is expected to adsorb to sediments or particulate matter and biodegrade. ready biodegradation reported to range from 0 to 100% in up to 28 days, probably at least inherently biodegradable; adaptation has been shown, if emitted to POTW on a regular basis (>3 times per week) assume readily biodegradable [3] Bioconcentration is not expected to occur.2 Bioconcentration factor 5-50, various fish species, 14-38 days, not bioaccumulating | aquatic organisms.1 Ecotoxicity Data: 1 freshwater: 96-hr LC50: 5 mg/L for rainbow trout (*Oncorhynchus mykiss*) 96-hr LC50: 8.18 mg/L for (fathead minnow (*Pimephales promelas*) (flow through test) 96-hr LC50: 11.8 mg/L for (Zebra fish) *Brachydanio rerio* (static test) 96-hr LC50: 4.5 mg/L for Japanese kill fish (*Oryzias latipes*) Additional ecotoxicity data[2] Algae: 72-hr EC50: 1.1 mg/L for biomass in *Scenedesmus subspicatus* 48-hr EC50: 5-10 mg/L for *Chlorella* emersonii, Chronic toxicity: NOEC: 0.82 mg/L (95-day early life-stage study) for fish Which fish, there are about 25'000 species? NOECs: 0.87 mg/L (21-day study) for *Daphnia magna*? NOEC: 0.37 mg/L for Algae (biomass in *Scenedesmus*) *subspicatus*, additional data available please document all for transparent derivation of PNEC, but definitive chronic PNEC for freshwater is 0.037 mg/L extrapolated marine PNEC 0.0037 mg/l (uncertain) |
| Safe Care1000 (SC-1000) | Light amber vegetable based detergent with pH approx. 10. Soluble in water. Non-ionic linear alcohol ethoxylate. Hydrophilic Lipophilic Balance (HLB): 13.85 favoring aqueous phase. MW: 224 g/mol A biobased complexing agent replaces EDTA. Imido sodium succinate | Biodegradable at 10 mg/L (67.5% by day 6) over a 28-day period. Non-biodegradable at 20 mg/L (37%) after 28 days.2 hence max daily use to be limited by POTW influent concentration not greater than 10 mg/l | Reported a non-toxic substance in the aquatic environment according to the MSDS. Ecotoxicity Data: 3 96-h LC50: ?? 66.5 µg/L ?? for fathead minnow (freshwater); 96-h LC50: 26.4 mg/L for *Menidia beryllina* (EPA approved-vertebrate for acute and chronic testing (marine) 48-hr LC50: 15.2 mg/L for *Mysidopsis* bahia (shrimp, used as a saltwater aquatic test organism) no other ecotox data located, insufficient for deriving a PNEC |
| Decyl Polyglucoside (CAS#68515-73-1) | Light yellow liquid, mildly non-ionic surfactant. Water soluble. It (CAS #68515-73-1) belongs to a bigger chemical group; alkyl polyglucoside (APG) surfactants. Examples are Decyl Glucoside ($C_{16}H_{32}O_6$, CAS#58846-77-8), Lauryl Glucoside ($C_{18}H_{36}O_6$, CAS#110615-47-9) | APG surfactants are readily biodegradable (modified OECD screening tests). APGs biodegrade in sewage systems.1 Alkylglucosides (C6, C8, C10 and C12) are readily biodegradable in both the Closed Bottle and Modified OECD Screening Tests | Not Available no other ecotox data located Alkylglucosides (C6, C8, C10) acute EC50 >500 mg/l and C12 EC50 >100 mg/l (>water solubility), 24 h *Daphnia magna*, more toxic for more hydrophobic substances (note only 24 h, insufficient duration) (Alkylglucosides no chronic data) |

TABLE 29-continued

Detergents analyzed

| Material | General characteristics | Biodegradability | Ecotoxity Data (Aquatic Tox) |
|---|---|---|---|
| | APGs do not contain phosphates, alkyphenol ethoxylates (APE), paradichlorobenzene, 1,4-dioxane, sodium hypochlorite, NTA or sodium EDTA1. Used in cosmetic formulations including baby shampoo and in sensitive skin products | Alkylpolyglucosides (mixtures) are readily biodegradable in both the Closed Bottle and Modified OECD Screening Tests | Alkylpolyglucosides (mixtures) acute EC50 ranging between 37 and 137 mg/l 24 h *Dapnhia magna*, more toxic for more hydrophobic mixtures (note only 24 h, insufficient duration) Alkylpolyglucosides (mixtures) chronic NOEC ranging between 1.4 and 4.3 mg/l 21 d *Daphnia magna*, more toxic for more hydrophobic mixtures insufficient data for PNEC marine light-emitting bacteria (very sensitive species, not often used nowadays, not normally used for derivation of PNEC): Alkylglucosides acute EC50: C6 = 490 mg/l; C8 = 11.7 mg/l; C10 = 7.9 mg/l; C12 = 8.8 mg/l), 30 min *Photobacterium phosphoreum*, more toxic for more hydrophobic substances Alkylpolyglucosides acute EC50 ranging between 5.9 and 16 mg/l, 30 min *Photobacterium phosphoreum*, more toxic for more hydrophobic substances insufficient data for PNEC |
| Decyl-beta-D glucopyranoside (CAS#58846-77-8) Also n-Decyl-beta-D glucopyranoside with CAS#59122-55-3 | Nonionic detergent White granular powder Chemical formulation: $C_{16}H_{32}O_6$ MW: 320.42 g/mol Commonly used in shampoos, body washes and hair color products. | No data available | No data available no other ecotox data located for both substances see above |
| Lauryl glucoside (CAS#110615-47-9) aka dodecyl glucoside | Mild surfactant Turbid viscous liquid[1] Chemical formulation: $C_{18}H_{36}O_6$ MW: 348.47 g/mol It is closely related to decyl glucoside, Used in cosmetics and produced from glucose and lauryl alcohol, used in personal care products (e.g., cleansers and shampoos). | No data available | No data available No other ecotox data See above |
| n-Octyl glucoside (CAS#29836-26-8) aka (Octyl β-D-glucopyranoside) | Nonionic detergent White granular powder Chemical formulation: $C_{14}H_{28}O_6$ | No data available | No data available No other ecotox data See above |
| Ecosurf EH-6 Ecosurf EH-9 (CAS#64366-70-7) [2-Ethyl Hexanol EO-PO Nonionic Surfactant, >99% (64366-70-7)] | A yellow liquid, dispersible in water Composed of more than 99% 2-Ethyl Hexanol EO-PO Nonionic Surfactant. Hydrophilic Lipophilic Balance (HLB) for EH9: 12.5 | Readily biodegradable per OECD 301F (greater than 60% at 28 d exposure time).1 Inherent biodegradability (OECD 302C) was confirmed[3] Ready biodegradability result comparable with DOW MSDS[3] | Aquatic toxicity reported as EC50 or LC50 on acute basis: between 10 and 100 mg/L. Acute Toxicity: 48-h EC50: 72.1 mg/L for water flea *Daphnia magna* 72-h EC50: 31.9-97.7 mg/L (geometric average 55.8 mg/L) for green algae (*Desmodesmus subspicatus*) Chronic Toxicity: 21-day NOEC: 31.6 mg/L for water flea *Daphnia magna* (OECD 211) |

TABLE 29-continued

Detergents analyzed

| Material | General characteristics | Biodegradability | Ecotoxity Data (Aquatic Tox) |
|---|---|---|---|
| | | | 72-h EC 10: 14.3 mg/L for algae (OECD 201) chronic freshwater PNEC 0.28 mg/l (note still some uncertainty as only two organism groups available) Extrapolated marine PNEC 0.028 mg/l |
| Ecosurf SA-7 Ecosurf SA-9 [Alcohols, C6-C12, ethoxylated, propoxylated, 55-80% (68937-66-6); Alcohols, C10-16, ethoxylated, propoxylated, 15-40% (69227-22-1); Poly(ethylene oxide), 1-2% (25322-68-3)] | Modified seed oil, alcohol ethoxylate with 7 ethylene oxide groups and 9 ethylene oxide groups, respectively. | Readily biodegradable per OECD 301F (greater than 60% at 28 d exposure time). | Aquatic toxicity reported as EC50 or LC50 on acute basis: between 10 and 100 mg/L. Acute Toxicity: 48-h EC50: 1.45-1.79 mg/L for water flea *Daphnia magna* 72-h EC50: 1.45-1.75 mg/L for green algae (*Desmodesmus subspicatus*) no other ecotox data located, insufficient for deriving a PNEC |
| Lutensol XL XL40, XL50, XL60, XL70, XL80 and XL90 (BASF) | Branched nonionic surfactants, alkyl polyethylene glycol ethers based on C10-Guerbet alcohol and ethylene oxide. Numeric portion of the product name indicates the general degree of ethoxylation. XL40, XL50, XL60, XL70, XL80 and XL90 are clear to cloudy liquids at room temperature. XL100 and XL140 are soft, colorless or slightly yellowish paste at 23° C. XL79, XL89 and XL99 are clear liquids at room temperature. Solubility in distilled or potable water varies from clear solution to insoluble depending on the product. pH range (at 5% aqueous)): 7 Average MW range: 380-860 g/mol | Over 60% biodegradation by day 28 (OECD 301B method - CO2 formation relative to the theoretical value). note this does not necessarily mean it is readily biodegradable according to all criteria, but it is inherently biodegradable | Acute toxicity for aquatic invertebrates (*Daphnia magna*): 48-h EC50: 1-10 mg/L for XL40 to XL50, 10-100 mg/L for XL60 to XL1001 Toxicity to aquatic plant (green algae): 72-h EC50: 10-100 mg/L for XL40 to XL1001 no other ecotox data located, insufficient for deriving a PNEC Lutensol XL90: LC50 >500 mg/l nominal concentration 96 h *Pimephales promelas* [Alpha Analytical Labs, Dec. 5, 2011] acute freshwater PNEC Lutensol XL90 = 0.01 mg/l, based on only range given for algae and daphnids (10-100 mg/l for both) extrapolated acute-based marine PNEC Lutensol XL90 = 0.001 mg/l |
| Lutensol XP XP30, XP40, XP50, XP60, XP69, XP70, XP79, XP80, XP89, XP90, XP99, XP100 and XP140. | Lutensol XP surfactants are alkyl polyethylene glycol ethers based on C10-Guerbet alcohol and ethylene oxide. Numeric portion of the product name indicates the general degree of ethoxylation (e.g., XP30 has 3 EO groups). XP30, XP40, XP50, XP60, XP70, XP80 and XP90 are clear to cloudy liquids at room temperature. XP100 and XP140 are soft, colorless or slightly yellowish paste at 23° C. XP69, XP79, XP89 and XP99 are clear liquid at room temperature. Solubility in distilled or potable water varies from clear solution to insoluble depending on the product. pH range (at 5% aqueous)): 7 Average MW range: 290-750 g/mol | Over 60% biodegradation by day 28 (OECD 301B method - $CO_2$ formation relative to the theoretical value).1 note this does not necessarily mean it is readily biodegradable according to all criteria, but it is inherently biodegradable | Acute toxicity for aquatic invertebrates (*Daphnia magna*): 48-h EC50: 1-10 mg/L for XP40 to XP50, 10-100 mg/L for XP60 to XP100, >100 mg/L for XP1401 Toxicity to aquatic plant (green algae): 72-h EC50: 10-100 mg/L for XP40 to XP100, over 100 mg/L for XP1401 no other ecotox data located, insufficient for deriving a PNEC Lutensol XP90: LC50 >500 mg/l nominal concentration 96 h *Pimephales promelas* [Alpha Analytical Labs, Dec. 5, 2011] acute freshwater PNEC Lutensol XP90 = 0.01 mg/l, based on only range given for algae and daphnids (10-100 mg/l for both) extrapolated acute-based marine PNEC Lutensol XP90 = 0.001 mg/l |

TABLE 29-continued

| Material | General characteristics | Biodegradability | Ecotoxity Data (Aquatic Tox) |
|---|---|---|---|
| Inoterra RAC | Nonionic surfactant used in rinse aid applications. Clear to yellow liquid, Water soluble pH: approx. 7 | Readily biodegradable ≥90% by modified OECD 303A >60% by OECD 301B1 | The product does not contain organically - bound halogen. Acute toxicity for aquatic invertebrates (*Daphnia. magna*): 48-h EC50: 10-100 mg/L.1 Toxicity to aquatic plant (green algae): 72-h EC50: 10-100 mg/L (OECD 201) no other ecotox data located, insufficient for deriving a PNEC |
| Natsurf 265 (CAS#27252-75-1) | Nonionic Surfactant Clear to hazy liquid\ Partially soluble in water pH: 5.5-7.0 Stable Hazardous decomposition includes oxides of carbon | Not available | Not Available no other ecotox data located, insufficient for deriving a PNEC |
| Chembetaine LEC Surfactant [lauramidopropyl betaine, 32% (4292-10-8), (Lubrizol)] | Chembetaine LEC surfactant is a high-purity, low color surfactant exhibiting excellent foam and viscosity building characteristics.1 Pale yellow clear liquid. Water soluble pH: 8-9 Used in moisturizing shampoo products. | Ultimately biodegradable1. lauramidopropyl betaine: readily biodegradable | Not available no other ecotox data located |
| APG 325N (CAS#132778-08-6) aka Decyl/Undecyl Glucoside | Yellowish to clear liquid Aqueous solution of alkyl poly glucosides based on synthetic fatty alcohol C9-C11. pH: 7-9.5, Soluble in water. Belongs to alkyl polyglucoside detergents, used in hard surface cleaners. | Per MSDS, Biodegradable to at least 90% on average per EU mandatory standards for detergents 82/242 (nonionic surfactants) and 82/243/EEC (anionic surfactants). | Acute Toxicity: LC50 >1-10 mg/L for fish Acute bacterial toxicity: EC0>100 mg/L (neat product) no other ecotox data located, insufficient for deriving a PNEC APG325N: LC50 >500 mg/l nominal concentration 96 h *Pimephales promelas* [Alpha Analytical Labs, Dec. 5, 2011] |
| Mackol DC (CAS#110615-47-9) | Yellow viscous liquid with characteristic odor Composition: 53-57% D-glucopyranose, oligomeric, decyl octyl glycoside and more than 47% water Water soluble Spec. gravity: 1.1 pH: 3-5 at 100% wt/wt % Used in shampoos, body washes, shower gels, facial cleansers | | No other ecotox data located |
| Triton CG-110 (CAS#68515-73-1) | Brown liquid aka Alkyl Polyglucoside Non-ionic surfactant Composition: 58-62% D-glucopyranose, oligomeric, decyl octyl glycoside and more than 38% water Water soluble Spec. gravity: 1.15 pH: 5.8 Molecular weight not available Applications: glass cleaners, highly alkaline detergents, food and dairy process cleaners, personal care products: shampoos, soaps, skin creams, lotions, hand dish detergents | Indicated as readily biodegradable >60% according to OECD 301F and OECD 311 >70% according to OECD 303A | For this family of materials: reported as non-toxic to aquatic organisms on an acute basis. LC50/EC50/LL50 >100 mg/L 96-h LC50 (static): 190-198 mg/L for fathead minnow 48-h EC50 (immobilization): 150-294 mg/L for water flea *Daphnia* m. 72-h ErC50 (growth rate inhibition): 189 mg/L for green algae (*Pseudokirchneriella subspicatus*) EC50 20 mg/l 48 h *Daphnia magna* EC50 21 mg/l 72 h *Selenastrum capricornutum* |

TABLE 29-continued

Detergents analyzed

| Material | General characteristics | Biodegradability | Ecotoxity Data (Aquatic Tox) |
|---|---|---|---|
| Tomadol@900 (CAS# 68439-46-3) | Clear liquid with mild odor Non-ionic surfactant Composition: 100% alcohol ethoxylate Contain no phenolic compounds3 Slightly water soluble, may form gel Spec. gravity: 0.98 pH (1% aq): 6.5 Molecular weight: 460 g/mol | Classified in EPA guidelines as readily biodegradable | acute-based freshwater PNEC 0.02 mg/l extrapolated marine PNEC 0.002 mg/l Aquatic Toxicity1: *Daphnia*: 1-10 mg/L Fish: 1-10 mg/L Based on comparison with similar products Aquatic Toxicity4: freshwater: 48-h EC50: 5.3 mg/L for *Daphnia* 96-h LC50: 8.5 mg/L for fathead minnow LC5 >5 mg/l nominal concentration (500 mg of a 1% aqueous solution per litre) 96 h *Pimephales promelas* chronic NOEC 1.01 mg/L 28 days *Pimephales promelas* Early Life Stage test chronic NOEC 2.04 mg/l 30 d on several invertebrate organism groups (Copepoda, Cladocera, Annelida, Nematoda, Diptera, Amphipoda) in a stream mesocosm remarks on algal toxicity in substance class, EC50 between 0.05 and 50 mg/l, but not usable for PNEC derivation chronic-based freshwater PNEC 0.02 mg/l, based on more than two organism groups but no primary producers, hence would strongly profit from algal and cyanobacterian growth tests. |

Five of the candidate materials were selected for further ecotoxicity studies:

Ecosurf EH-9

Triton CG-110

Tomadol

APG 325

Lutensol XP-90

The purpose of the ecotoxicity studies was to establish for each candidate material the highest concentration at which the candidate material would present no significant risk to aquatic organisms. This concentration is referred to as the predicted no effect concentration (PNEC), and the methods used to develop specific PNECs for the candidate materials is detailed in the European Union's Technical Guidance Document for Risk Assessment, 2003 (TGD).

To develop the PNECs, each of these five candidate materials were evaluated using the Organization for Economic Co-Development's (OECD) test methods for determining activated sludge respiration inhibition (OECD 209), algal growth inhibition (OECD 201), daphnid acute immobilisation (OECD 202), daphnid chronic reproduction (OECD 211) and fish acute toxicity assays (OECD 203).

These studies yielded both a PNEC for the wastewater treatment plants receiving the process wastewater, the $PNEC_{STP}$, and a PNEC for the receiving water body, the $PNEC_{RW}$.

The use of the candidate materials at the manufacturing sites would result in concentrations of the candidate materials in both the wastewater treatment plants, referred to as the predicted environmental concentration for the sewage treatment plant ($PEC_{STP}$), and the receiving water bodies, referred to as the predicted environmental concentration for the receiving waters ($PEC_{RW}$). The wastewater treatment plants also remove a portion of the candidate materials from the wastewater, an amount that was calculated for each of the candidate materials through testing using the OECD's ready biodegradability test (OECD 301F)

This comparison of the PECs with the PNECs for the five candidate materials provides a useful environmental compatibility profile. A candidate material was considered to be environmentally compatible when its PEC was lower than its PNEC.

What is claimed is:

1. A method of inactivating virus in a product feedstream in a manufacturing process of a therapeutic polypeptide, the method comprising the step of subjecting the feedstream to a detergent, wherein the detergent is environmentally compatible, wherein the environmentally compatible detergent has a CAS registry number of CAS 68515-73-1, CAS 58846-77-8, CAS 59122-55-3, CAS 110615-47-9, CAS 64366-70-7, CAS 68937-66-6, CAS 69227-22-1, CAS 27252-75-1, or CAS 132778-08 6.

2. The method of claim 1, wherein the method maintains product quality of the therapeutic polypeptide compared to a method using Triton X-100 or a method without detergent.

3. The method of claim 2, wherein the therapeutic polypeptide's product quality results in no more than a 5% change in product variants out of the total polypeptide in the product feedstream.

4. The method of claim 3, wherein the product variants do not increase by more than 5% out of the total polypeptide in the product feedstream.

5. The method of claim 3, wherein the product variants are size variants, charge variants, oxidation variants, deamidation variants, glycation variants or variants with altered glycan profiles.

6. The method of claim 3, wherein the product variants are acidic and/or basic product variants.

7. The method of claim 1, wherein subjecting the feedstream to detergent does not increase fragmentation of the polypeptide by more than about 5%.

8. The method of claim 1, wherein subjecting the feedstream to detergent does not increase aggregation in the feedstream by more than about 5%.

9. The method of claim 1, wherein subjecting the feedstream to detergent does not reduce the yield of the polypeptide in the manufacturing process by more than about 5%.

10. The method of claim 1, wherein the detergent is added to the feedstream to a final concentration of about 0.01% to about 10%.

11. The method of claim 1, wherein the detergent is added to the feedstream to a final concentration of about 0.3% to about 1%.

12. The method of claim 1, wherein the feedstream is subjected to the detergent for at least about 1 minute to at least about 48 hours.

13. The method of claim 1, wherein the feedstream is subjected to the detergent for at least about 15 minutes to at least about 3 hours.

14. The method of claim 1, wherein the feedstream is subjected to the detergent for at least about 1 hour.

15. The method of claim 1, wherein the feedstream is subjected to the detergent at about 4° C. to about 30° C.

16. The method of claim 1, wherein the feedstream is subjected to the detergent at about 15° C. to about 20° C.

17. The method of claim 1, wherein the detergent is a non-ionic detergent or zwitterionic detergent.

18. The method of claim 1, wherein the detergent has a hydrophile lipophile balance (HLB) from about 12 to about 15.

19. The method of claim 1, wherein the detergent does not comprise or form octylphenol.

20. The method of claim 1, wherein the detergent does not comprise or form peroxide.

21. The method of claim 1, wherein the feedstream comprising the detergent is of low turbidity.

22. The method of claim 1, wherein addition of the detergent to the feedstream does not increase the turbidity of the feedstream.

23. The method of claim 1, wherein upon disposal the detergent's Predicted Environmental Concentration (PEC) in the receiving water body resulting from use of the detergent is below the Predicted No-Effect Concentration (PNEC) of the detergent.

24. The method of claim 23, wherein the PEC is lower than the PNEC.

25. The method of claim 1, wherein the detergent comprises one or more surfactants.

26. The method of claim 1, wherein the detergent comprises one or more surfactants, preservatives, and chelating agents.

27. The method of claim 1, wherein the feedstream comprises a harvested cell culture fluid.

28. The method of claim 27, wherein the detergent is added to the harvested cell culture fluid.

29. The method of claim 1, wherein the feedstream comprises a capture pool or a recovered product pool.

30. The method of claim 29, wherein the capture pool or recovered product pool is an affinity chromatography pool.

31. The method of claim 29, wherein the capture pool or recovered product pool is a protein A pool, a protein G pool or a protein L pool.

32. The method of claim 29, wherein the capture pool or recovered product pool is a mixed mode chromatography pool.

33. The method of claim 1, wherein the detergent is used in combination with an anti-foaming agent.

34. The method of claim 33, wherein the antifoaming agent is simethicone.

35. The method of claim 1, wherein the virus is an enveloped virus.

36. The method of claim 1, wherein the virus is a retrovirus, a herpesvirus, a flavivirus, a poxvirus, a hepadnavirus, a hepatitis virus, an orthomyxovirus, a paramyxovirus, a rhabdovirus, or a togavirus.

37. The method of claim 1, where in the viral log reduction value (LRV) of the detergent in the feedstream is greater than about one.

38. The method of claim 1, wherein the viral LRV is greater than about four.

39. The method of claim 37, wherein the LRV is calculated based on infectivity assay.

40. The method of claim 39, wherein the infectivity assay is a plaque assay or a $TCID_{50}$ assay.

41. The method of claim 1, wherein the method further comprises a step of filtering the feedstream after adding the detergent.

42. The method of claim 41, wherein the feedstream is filtered at least about 15 minutes to at least about 48 hours after addition of the detergent.

43. The method of claim 41, wherein the feedstream is filtered at least about 1 hour to at least about 3 hours after addition of the detergent.

44. The method of claim 41, wherein the feedstream is filtered after about 1 hour after addition of the detergent.

45. The method of claim 41, wherein the filter is an ultrafilter or a depth filter.

46. The method of claim 1, wherein the feedstream is subjected to chromatography after addition of the detergent.

47. The method of claim 46, wherein the chromatography is one or more of an affinity chromatography, an ion exchange chromatography a hydrophobic interaction chromatography, a hydroxyapatite chromatography, or a mixed mode chromatography.

48. The method of claim 47, wherein the affinity chromatography is a protein A chromatography, a protein G chromatography or a protein L chromatography.

49. The method of claim 47, wherein the ion exchange chromatography is an anion exchange chromatography or a cation exchange chromatography.

50. The method of claim 1, wherein the therapeutic polypeptide is an antibody, an immunoadhesin, an enzyme, a growth factor, a receptor, hormone, a regulatory factor, a cytokine, an Fc fusion polypeptide, an antigen, or a binding agent.

51. The method of claim 50, wherein the antibody is a monoclonal antibody, a chimeric antibody, a humanized antibody, a human antibody, a bispecific antibody, or an antibody fragment.

52. The method of claim 1, wherein the therapeutic polypeptide is produced in mammalian cells.

53. The method of claim 52, wherein the mammalian cell line is a Chinese Hamster Ovary (CHO) cells, or baby hamster kidney (BHK) cells, murine hybridoma cells, or murine myeloma cells.

54. The method of claim 1, wherein the environmentally compatible detergent has a CAS registry number of CAS 110615-47-9.

55. The method of claim 1, wherein the environmentally compatible detergent has a CAS registry number of CAS 68515-73-1.

* * * * *